United States Patent
Suenaga et al.

(10) Patent No.: US 9,422,315 B2
(45) Date of Patent: Aug. 23, 2016

(54) ORGANOSILOXANE COMPOSITION HAVING HIGH REFRACTIVE INDEX AND APPLICATIONS CONTAINING THE SAME

(71) Applicant: Momentive Performance Materials Japan LLC, Tokyo (JP)

(72) Inventors: Koji Suenaga, Gunma (JP); Amar Pawar, Elmsford, NY (US); Benjamin Falk, Yorktown Heights, NY (US)

(73) Assignee: Momentive Performance Materials Japan LLC, Tokyo (JP)

(*) Notice: Subject to any disclaimer, the term of this patent is extended or adjusted under 35 U.S.C. 154(b) by 46 days.

(21) Appl. No.: 14/561,371

(22) Filed: Dec. 5, 2014

(65) Prior Publication Data

US 2016/0159829 A1    Jun. 9, 2016

(51) Int. Cl.

| | |
|---|---|
| C07F 7/08 | (2006.01) |
| A61K 8/58 | (2006.01) |
| A61Q 17/04 | (2006.01) |
| A61Q 1/02 | (2006.01) |
| A61Q 1/06 | (2006.01) |
| A61Q 1/10 | (2006.01) |
| A61Q 5/02 | (2006.01) |
| A61Q 5/12 | (2006.01) |
| A61Q 1/04 | (2006.01) |
| A61K 8/81 | (2006.01) |

(Continued)

(52) U.S. Cl.
CPC ............... *C07F 7/0849* (2013.01); *A61K 8/58* (2013.01); *A61K 8/585* (2013.01); *A61K 8/81* (2013.01); *A61K 8/891* (2013.01); *A61Q 1/02* (2013.01); *A61Q 1/04* (2013.01); *A61Q 1/06* (2013.01); *A61Q 1/10* (2013.01); *A61Q 5/02* (2013.01); *A61Q 5/12* (2013.01); *A61Q 17/04* (2013.01); *A61Q 19/00* (2013.01); *C07F 7/21* (2013.01); *A61K 2800/10* (2013.01)

(58) Field of Classification Search
CPC ...... C07F 7/0849; A61K 8/585; A61Q 1/10; A61Q 17/04; A61Q 5/02; A61Q 5/12
USPC ............................................. 556/456; 514/63
See application file for complete search history.

(56) References Cited

U.S. PATENT DOCUMENTS

| | | |
|---|---|---|
| 2,444,555 A | 9/1945 | Daudt |
| 2,754,284 A | 7/1956 | Speck |

(Continued)

FOREIGN PATENT DOCUMENTS

| | | |
|---|---|---|
| JP | H0789844 A | 4/1995 |
| JP | 2001307379 A | 11/2001 |

(Continued)

OTHER PUBLICATIONS

J.L. Spier, "Homogeneous Catalysis of Hydrosilation by Transition Metals, In Advances in Organometallic Chemistry", vol. 17, (1979) pp. 407-447, F.G.A. Stone & R. West Editors, Academic Press.

(Continued)

*Primary Examiner* — Porfirio Nazario Gonzalez
(74) *Attorney, Agent, or Firm* — Joseph S. Ostroff

(57) ABSTRACT

The invention is directed to a silicone compound of the general formula (I) and a personal care composition comprising the silicone compound (I) as described herein, and to personal care applications containing the same and processes of making the silicone compound.

28 Claims, 1 Drawing Sheet

(51) Int. Cl.
  *A61Q 19/00* (2006.01)
  *A61K 8/891* (2006.01)
  *C07F 7/21* (2006.01)

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,715,334 A | 2/1973 | Karstedt | |
| 3,775,452 A | 11/1973 | Karstedt | |
| 3,814,730 A | 6/1974 | Karstedt | |
| 5,539,137 A | 7/1996 | Lewis et al. | |
| 5,684,112 A | 11/1997 | Berthiaume et al. | |
| 6,225,467 B1 | 5/2001 | Esteghamation et al. | |
| 8,263,720 B1* | 9/2012 | Salamone | A61L 26/0019 424/443 |
| 2007/0041935 A1 | 2/2007 | Salamone et al. | |
| 2013/0023591 A1 | 1/2013 | Shoji et al. | |

FOREIGN PATENT DOCUMENTS

| | | |
|---|---|---|
| JP | 2004/256660 A | 9/2004 |
| WO | 02/051828 A | 7/2002 |
| WO | 2004/055081 A | 7/2004 |
| WO | 2004/085412 | 8/2004 |
| WO | 2006/034982 | 4/2006 |
| WO | 2006/034985 | 4/2006 |
| WO | 2006/034991 | 4/2006 |
| WO | 2006/034992 | 4/2006 |
| WO | 2006/035000 | 4/2006 |
| WO | 2006/035007 | 4/2006 |
| WO | 2009/032266 A2 | 3/2009 |
| WO | 2010/121024 A2 | 10/2010 |
| WO | 2011/081218 A1 | 7/2011 |
| WO | 2013/191305 A1 | 12/2013 |

OTHER PUBLICATIONS

J.L. Spier, "Homogeneous Catalysis of Hydrosilation by Transition Metals, In Advances in Organometallic Chemistry", vol. 17, (1979) pp. 407.447, F.G.A. Stone & R. West Editors, Academic Press.
Sharma, et al., "(Me3N)Mo(CO)5-Catalyzed Reduction of DMF by Disiloxane and Disilane Moieties: Fate of the Silicon-Containing Fragments", Organometallics, vol. 32, Issue 14, pp. 3788-3794.
Spek, et al., "3. 3-Dimethyl-1, 1, 1,5,5,5-hexaphenyltrisiloxane", Acta Crystallographica, Section E: Structure Reports Online, vol. 61, Issue: 10, pp. o3324-03326.
Andrianov, et al., "X-ray diffraction studies of some spirocyclic and cross-shaped organometallic compounds", Izvestiya Akademii Kauk SSSR, Seriya Khimicheskaya, issue 10, Journal (1971) pp. 2145-2150.
Andreev, et al., "Organosilyl acrylates" Zhurnal Obshohei Khimii, vol. 36, Issue 4, Journal (1996) pp. 692-694.
Borisov, et al, "Reaction of silanois with hydrosilanes", Zhurnal Obshchei Khimii, vol. 36, Issue 4, Journal (1966) pp. 687-692.
Zhdanov, et al., "Synthesis of 3.4-benzo-1, 1-dichloro-1-silacyclohexane and some of its derivatives", Zhurnal Obshchei Khimii, vol. 36, Issue 3, Journal (1966) pp. 521-525.
Takiguchi, et al., "Preparation of several triphenylsiloxysilanes", Bulletin of the Chemical Society of Japan, vol. 39, Issue 3, Journal (1966) pp. 619-620.
Hora, et al., "Molecular spectra of methylphenylsiloxanes", Khim. i Prakt Primenenie Kremneorg. Soedinenii, Trudy Konf., Leningrad, vol. 1958, Issue No. 6, Journal (1961) pp. 272-277.
Horak, et al., "Organosilicon compounds. XVI Molecular spectra of methyl phenyl siloxanes", Collection of Czechoslovak Chemical Communications, vol. 24, Journal (1959) pp. 3381-3388.
Horak, et al., "Organosilicon compounds. XVI. Molecular spectra of methyl phenyl siloxanes", Chemicke Listy pro Vedu a Prumysl vol. 52, Journal (1958) pp. 2048-2055.
Gillman, et al., "An allyl displacement of a benzyl group fromm di- and tribenzylsilane", Journal of the American Chemical Society, vol. 81, Journal (1959) pp. 137-139.
Bazant, et al., "Organo-silicon compounds XV. Preparation of linear methylphenyltetrasiloxanes", Collection of Czechoslovak Chemical Communications, vol. 24. Journal (1959) pp. 624-629.
Hazell, et al., "Reaction of 2,2-diphenyl-1-picrylhydeazyl with secondary amines", Canadian Journal of Chemistry, vol. 36, Journal (1958) pp. 1729-1734.
Beringer, et al., "Diaryliodonium salts VIII Decomposition of substituted diphenyliodonium halides in inert solvents", Journall of American Chemical Society, vol. 80, Journal (1958) pp. 4535-4536.
Bazant, et al., "Organosilicon compunds. XV Preparation of linear methylphenyltetrasiloxanes", Chemicke Listy pro Vedu a Prumysl, vol. 52, Journal (1958) pp. 1751-1751.
V.S. Chugunov. "Synthesis of triphenylemethyl and triphenylethyl siloxanes", Izvestiya Akademii Nauk SSSR, Senya Khimicheskaya, Journal (1957) pp. 1368-1370.
S B. Speck, "Silicon-containing condensation polymers", Journal of Organic Chemistry. vol. 18, Journal (1953) pp. 1689-1700.
Gilman, et al., Steric hindrance in highly-substituted organosilicon compunds, III. The preparation and properties of some triarylsilyl ethers, Journal of Organic Chemistry, vol. 19, Journal (1954) pp. 441-450.
Kraft, et al., "Polymeric arseno compounds, III. Preparation of various polymer homologs of Salvrsan by reduction of 3-nitro(or amino)-4-hydroxyphenylarsonic acid by sodium hydrosulfite", Sbornik Statei po Obshchei Khimii, vol. 2, Journal (1953) pp. 1360-1365.
Shimizu et al., "Cosmetics based on a silsesquioxane resin, a hydrocarbon-based resin, and nonvolatile hydrocarbon and silicone oils", XP002754968, retrieved from STN Database accession No. 2013:1996607.
Stabler et al., "Silicone-peroxide compositions for long-term, controlled oxygen release", XP002754969, retrieved from STN Database accession No. 2010:1316803.
Chauhan et al., "Dispersions of polymeric microparticles and microgels in hydrogels for opthalmic drug delivery", XP002754970, retrieved from STN Database accession No. 2009. 293882.
Park et al., "Ir(I)/HCl Catalyzed Head-to-Tall Homocoupling Reactions Vinylsilanes", Organic Letters, vol. 14, No. 6, Mar. 16, 2012, pp. 1468-1471, XP055252316.
Park et al., "Ir(I)/HCl Catalyzed Head-to-Tall Homocoupling Reactions Vinylsilanes—Supplementary Informaiton", Organic Letters, vol. 14, No. 6, Jan. 1, 2012, pp. S1-S33, compound (1i), p. S3, para 2-3.
Gadda et el., "Synthesis and characterization of alt-copoly (carbosiloxane)s containing oligodiphenylsiloxane segments", Journal of Polymer Science Part A Polymer Chemistry, vol. 43, No. 10, Apr. 8, 2005, pp. 2155-2163, XP055252313.
Chrusciel et al., "Dehydrocondensation of Organic Hydrosilanes with Silanols Part II Effect of Siloxane Chain Length on the Reactivity of Sl-H End-Groups. The Substitution Effect", Polish Journal of Chemistry, vol. 57, No. 1/3, (1983), pp. 121-128.
Horac et al., Collection of Czechoslovak Chemical Communications; vol. 24, (1959), pp. 3381-3384.
Gusev et al., "Crystal and Molecular Structure of Triphenyltrivinyldisloxane" Journal of Structural Chemistry, vol. 25, (1984), pp. 154-106.
Andrianov et al., Bulletln of the Academy of Sciences of the USSR, Division of Chemical Science (Eng. Trans ), (1962). pp 1487-1491.
Andrianov et al., Bulletin of the Academy of Sciences of the USSR, Division of Chemical Science (Eng. Trans.), vol. 20, (1971), pp. 1991-1995.
Liu et al., "Synthesis and application of moisture-stable methallylsilanated phosphorylcholine as a surface modifier" Tetrahedron Letters, vol. 55, No. 45, Sep. 20, 2014, pp. 6245-6247, XP029080079.
International Search Report dated Mar. 16. 2010.

* cited by examiner

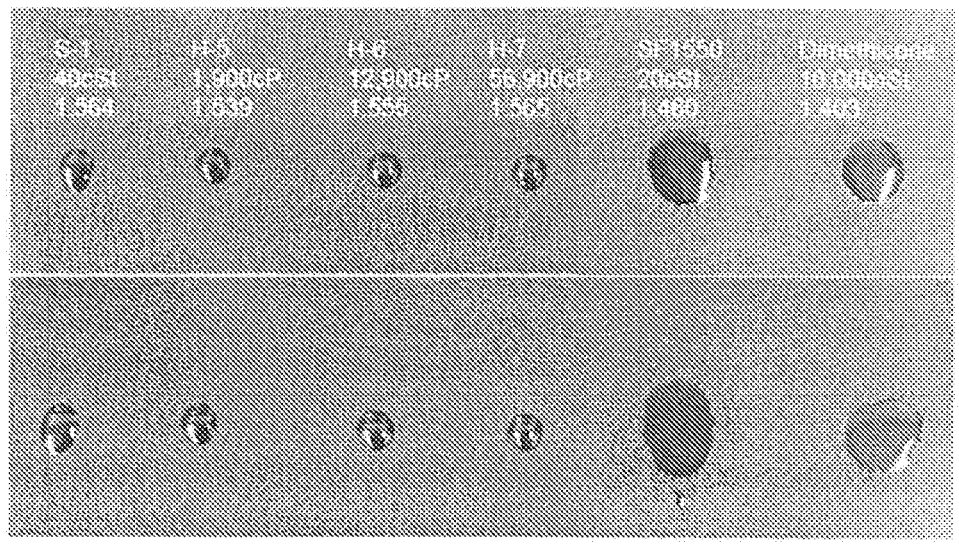

ORGANOSILOXANE COMPOSITION HAVING HIGH REFRACTIVE INDEX AND APPLICATIONS CONTAINING THE SAME

FIELD OF THE INVENTION

The present invention relates to silicone compositions, specifically silicone compositions with high refractive indices and personal care applications comprising the same, as well as processes for making the same.

BACKGROUND OF THE INVENTION

Silicones have properties that make them particularly advantageous in personal care products. Certain silicones produce uniform thin films that are hydrophobic and also produce solutions or emulsions that posses a low viscosity. The low viscosity property allows higher loadings of active ingredients in a cosmetic product without the deleterious effects normally associated with high viscosity products.

In addition, the personal care industry has produced a wide-range of hair care and cosmetic applications that utilize silicones. Among the various products are shampoos to clean the hair and scalp, hair rinses, conditioners, dressings, sprays, coloring and bleaching preparations, permanent waves, and hair straightening and strengthening compositions. Consumers desire a shampoo that foams quickly and copiously and rinses thoroughly leaving the hair with a fresh clean smell and in a manageable state. Further, consumers tend to prefer those shampoos that also leave the hair soft, shiny, lustrous, and full bodied. After shampooing, the hair is usually wet, frequently tangled and thus difficult to comb. Thus it is common for consumers to apply rinses and conditioners to enhance the ease of combing and detangling, to increase hair body, to improve shine and texture, to prevent static buildup, to impart manageability, style retention, and curl retention.

One method of imparting or increasing apparent luster or gloss on the hair is to coat the hair with a material having a high refractive index. Using this technique, the apparent gloss or shine will be proportional to the refractive index of the material on she fiber surface. Absent other factors, a direct proportionality exists between refractive index and apparent shine on hair. Thus higher refractive index cuticle coating formulations will tend to impart a higher shine on hair.

SUMMARY OF THE INVENTION

The invention is directed to silicone compound(s) which are 1,1,1-triphenyl-3,3-dialkyl-3-alkenyldisiloxane(s) or to silicone compounds which contain a 1,1,1-triphenyl-3,3-dialkyl-3(–)disiloxane moiety. Such silicone compounds have been unexpectedly found to have high refractive indices, which provide decreased migration, improved luster and improved shine for personal care applications.

In one non-limiting embodiment herein there is provided a silicone compound of the general formula (I) A silicone compound having a structure of general formula (I):

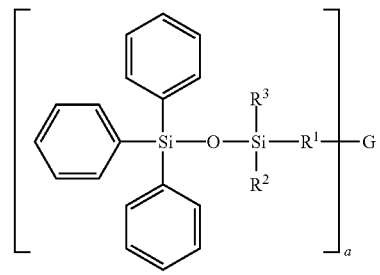

where each $R^2$ and each $R^3$ are independently selected from a monovalent hydrocarbon radical containing from 1 to about 8 carbon atoms, each $R^1$ is a divalent alkyl, alkene, arylene or alkyne group, each containing up to about 45 carbon atoms, more specifically up to about 30 carbon atoms, even more specifically up to about 20 carbon atoms, and most specifically up to 12 carbons, and in one non-limiting embodiment, the lower endpoint of such ranges can comprise any one of 1, 2, 3, 4, 8, and 12 when the $R^1$ is a divalent alkyl, and any one of 2, 3, 4, 5, and 6 when $R^1$ is a divalent alkylene or alkyne, and any one of 6, 7 or 8 when $R^1$ is a divalent arylene, and G is hydrogen, an organic group or a silicon-containing group, and where subscript a is an integer of from 1 to 100, more specifically from 1 to about 50, even more specifically from 1 to about 20 and most specifically from 1 to about 6. In one non-limiting embodiment $R^1$ is a divalent alkyl, alkene, arylene or alkyne group, each containing from 2 to 45 carbon atoms, more specifically from 2 to 30 carbon atoms, and most specifically, from 2 to 15 carbon atoms. In one more non-limiting embodiment G is an organic group of irons 1 to 8 carbon atoms, more specifically from 2 to 8 carbon atoms and most specifically from 4 to 6 carbon atoms.

In one other embodiment herein there is provided a personal care composition comprising the silicone compound of the general formula (I) as described herein.

In yet another embodiment herein there is provided a process of making a 1,1,1-triphenyl-3,3-dialkyl-3-alkenyldisiloxane comprising reacting triphenylsilanol with a 1,1,3,3-tetralkyl-1,3-dialkenyldisilazane and/or an alkenyldialkylhalosilane to produce 1,1,1-triphenyl-3,3-dialkyl-3-alkenyldisiloxane, wherein each of the alkyl groups independently contain front 1 to 6 carbon atoms and each of the alkenyl groups independently contain from 2 to 4 carbon atoms.

BRIEF DESCRIPTION OF THE DRAWING

FIG. 1 is a photograph showing the non-migration properties of organosiloxanes S-1 and H-5 to H-7 as described below.

DETAILED DESCRIPTION OF THE INVENTION

The inventors herein have unexpectedly discovered a silicone compound which is a 1,1,1-triphenyl-3,3-dialkyl-3-alkenyldisiloxane or a silicone compound containing a 1,1,1-triphenyl-3,3-dialkyl-3(–)disiloxane moiety, and wherein such compounds provide for high refractive indices, e.g., in excess of 1.5, possess non migrating properties and which compound(s) may be employed in personal care applications.

Other than in the working examples, or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursory. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

As stated herein all temperatures are in Celsius and viscosities are measured at 25 degrees Celsius and when viscosity is recited in using centistokes (cSt) that viscosity was measured using Cannon-Fenske viscometer and when viscosity is measured use centipoise (cP) that viscosity was measured using Vismetron viscometer, VSA-L model (which is similar to a Blookfield viscometer, LVT model).

As used herein the term "alkyl" means a saturated straight or branched monovalent hydrocarbon radical. In a preferred embodiment, monovalent alkyl groups are selected from linear or branched alkyl groups containing from 1 to 6 carbons per group, such as, for example, methyl, ethyl, propyl, iso-propyl, n-butyl, iso-butyl sec-butyl tert-butyl, pentyl, iso-pentyl, neopentyl, tert-pentyl 2,2,4-trimethylpentyl and hexyl.

As used herein the term "alkenyl" means a straight or branched monovalent terminally unsaturated hydrocarbon radical, specifically containing from 2 to 4 carbon, atoms per radical, such as, for example, vinyl, 2-propenyl and 3-butenyl.

As used herein, the expression "divalent alkylene radical" means a saturated straight or branched divalent hydrocarbon radical. Suitable divalent alkylene radicals include, for example, linear or branched alkylene radicals, such as, for example, methylene, dimethylene, trimethylene, 2-methyltrimethylene and 2,2-dimethyltrimethylene.

As used herein, a "personal care composition" is a composition comprising the silicone compound described herein and any component or ingredient of a personal care application.

A "personal care application" as used herein is understood to be a consumer product used for personal hygiene and/or personal beautification.

In one non-limiting embodiment the silicone compound having a structure of general formula (I) is such as described herein but where G is selected from the group consisting of:
  a) an organic group that is a linear or branched, unsaturated or saturated hydrocarbon radical containing up to about 1,000 carbon atoms, more specifically up to about 500 carbon atoms, even more specifically up to about 100 carbon atoms, yet even more specifically up to about 30 carbon atoms, and optionally containing at least one of a heteroatom, a carbonyl group, an ester group, an amide group and a hydroxyl group with a valency of 1-25, more specifically from 1 to about 15, and most specifically from 1 to about 6, subject to the limitation that the valance of the organic group is equal to the value of the subscript a;

b) a cyclic siloxane with the general formula (II):

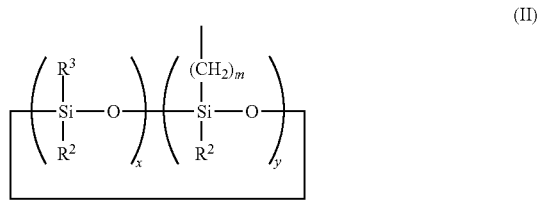

each $R^2$ and each $R^3$ are independently a monovalent hydrocarbon radical containing from 1 to about 8 carbon atoms, more specifically from 1 to about 6 carbon atoms and most specifically from 1 to about 4 carbon atoms, the subscript m is an integer of from 2 to 6, more specifically 2 to 3, and the subscript x is 0 to about 8, more specifically an integer of from 1 to about 6 and most specifically from 1 to about 3, and the subscript y is an integer of from 1 to 8, more specifically from 1 to about 6, and most specifically from 1 to about 3, subject to the limitation that the value of subscript a=y; and, c) a siloxane with the general formula (III):

$$M_b M^*_c D_d D^*_e T_f T^*_g Q_h A_i B_j C_k \quad (III)$$

where
$M=R^4R^5R^6SiO_{1/2}$,
$M^*=R^4R^*R^6SiO_{1/2}$,
$D=R^7R^8SiO_{1/2}$,
$D^*=R^7R^*SiO_{1/2}$,
$T=R^9SiO_{3/2}$,
$T^*=R^*SiO_{3/2}$,
$Q=SiO_{4/2}$,
$A=O_{1/2}Si(R^{10})(R^{11})R^{12}Si(R^{13})(R^{14})O_{1/2}$
$B=O_{1/2}Si(R^{15})(R^{16})R^{17}Si(R^{18})O_{2/2}$
$C=O_{1/2}Si(R^{19})(R^{20})R^{21}SiO_{3/2}$ where $R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$, and $R^{20}$ are each independently selected from, the group consisting of $OR^{22}$ find a monovalent hydrocarbon radical containing from 1 to about 20 carbon atoms, more specifically from 1 to about 12 carbon, atoms and most specifically from 1 to about 6 carbon atoms, optionally containing at least one of a heteroatom e.g., O, N or S, an aromatic group of from 6 to about 10 carbon atoms, and a hydroxyl group, $R^{12}$, $R^{17}$, and $R^{21}$ are independently a divalent hydrocarbon group of from 1 to about 8 carbon atoms, more specifically from 1 to about 4 carbon atoms, $R^{22}$ is a monovalent hydrocarbon of from 1 to about 20 carbon atoms, more specifically from 1 to about 12 carbon atoms and most specifically from 1 to about 6 carbon atoms, $R^*$ is a divalent hydrocarbon of from 1 to about 8 carbon atoms, more specifically from 1 to about 6 carbon atoms and most specifically from 1 to about 4 carbon atoms, where one of the valences of $R^*$ is bound to $R^1$, and subscripts b, c, d, e, f, g, h, i, j and k are zero or positive subject to the limitation b+c+d+e+f+g+h+i+j<1000, more specifically b+c+d+e+f+g+h+i+j<750, even more specifically b+c+d+e+f+g+h+i+j<500 and most specifically b+c+d+e+f+g+h+i+j<100, wherein the lower endpoints of any of said ranges of b+c+d+e+f+g+h+i+j can be any one or more of 1, 2, 3, 5, 10, 12, 20, 50 or 60, and c+e+g≥1, more specifically c+e+g≥2, even more specifically c+e+g≥3 and upper end points to such ranges of c+e+g can be any one of 4, 5, 8, 10, 12, 20, 50, 60 or 100, and c+e+g=a.

In one non-limiting embodiment herein, $R^1$ of general formula (I) is independently more specifically, a divalent alkyl group containing from one to 6 carbon atoms, more specifically from 1 to 4 carbon atoms and most specifically from 1 to 3 carbon atoms, such as the non-limiting examples of alkyl described herein, and such as the non-limiting example of divalent methyl, ethyl propyl or isopropyl.

In one non-limiting embodiment herein the definition of $R^1$ of the general formula (I) is dependent on the value of the subscript a. If a=1, then in one non-limiting embodiment $R^1$ is a divalent unsaturated alkenyl group of from 2 to about 4 carbon atoms, such as those examples of alkenyl described herein, and more specifically such as the non-limiting example of vinyl, and G in one non-limiting embodiment is a hydrogen atom terminating $R^1$ when $R^1$ is a divalent alkene group. In another non-limiting embodiment if a=1, then $R^1$ is a divalent alkyl group containing from 1 to about 6 carbon atoms, more specifically from 1 to about 4 carbon atoms, even more specifically front 1 to about 3 carbon atoms, such as the non-limiting examples of alkyl described herein, and such as the non-limiting example of divalent methyl, ethyl, propyl and isopropyl and G in one non-limiting embodiment is a hydrogen atom terminating $R^1$ when $R^1$ is a divalent alkyl group. It will be understood that the aforementioned ranges of chain length for alkyl can also have a lower endpoint of 2 carbon atoms.

In one non-limiting embodiment, herein the silicon-containing group in the definition of G in formula (I) is a silicone-Containing group of from 1 to about 20 silicon atoms, more specifically from 1 to about 18 silicon atoms, more specifically from 1 to about 12 silicon atoms and most specifically from 1 to about 8 silicon atoms, wherein said ranges can in one non-limiting embodiment have any one of 2, 3, or 4 silicon atoms.

In yet a further non-limiting embodiment herein, the silicone compound of the formula (I) is such that a=1 and $R^1$ is a linear or branched unsaturated hydrocarbon radical of up to 8 carbon atoms, more specifically up to 6 carbon atoms, and most specifically up to 3 carbon atoms, e.g., vinyl, wherein in another embodiment G is hydrogen to terminate $R^1$ when $R^1$ is divalent alkylene.

In one non-limiting embodiment herein the silicone compound of formula (I) can be of the general formula (IV):

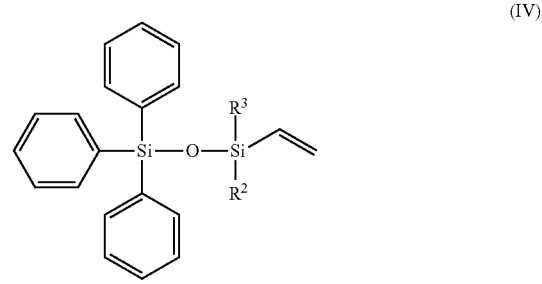

wherein each $R^2$ and $R^3$ are independently as defined herein, and more specifically each $R^2$ and $R^3$ are independently an alkyl group of from 1 to 3 carbon atoms.

In yet another embodiment herein the silicone compound of the general formula (I) is of the general formula (III) as described herein and the subscripts i+j+k≥1, more specifically i+j+k≥2, even more specifically, i+j+k≥3 and in other embodiments such ranges can have upper endpoints of any one of 5, 6, 8, 10, 12, 15, 20 or 50.

In yet another embodiment herein the silicone compound of the general formula (I) can be selected from the group consisting of:

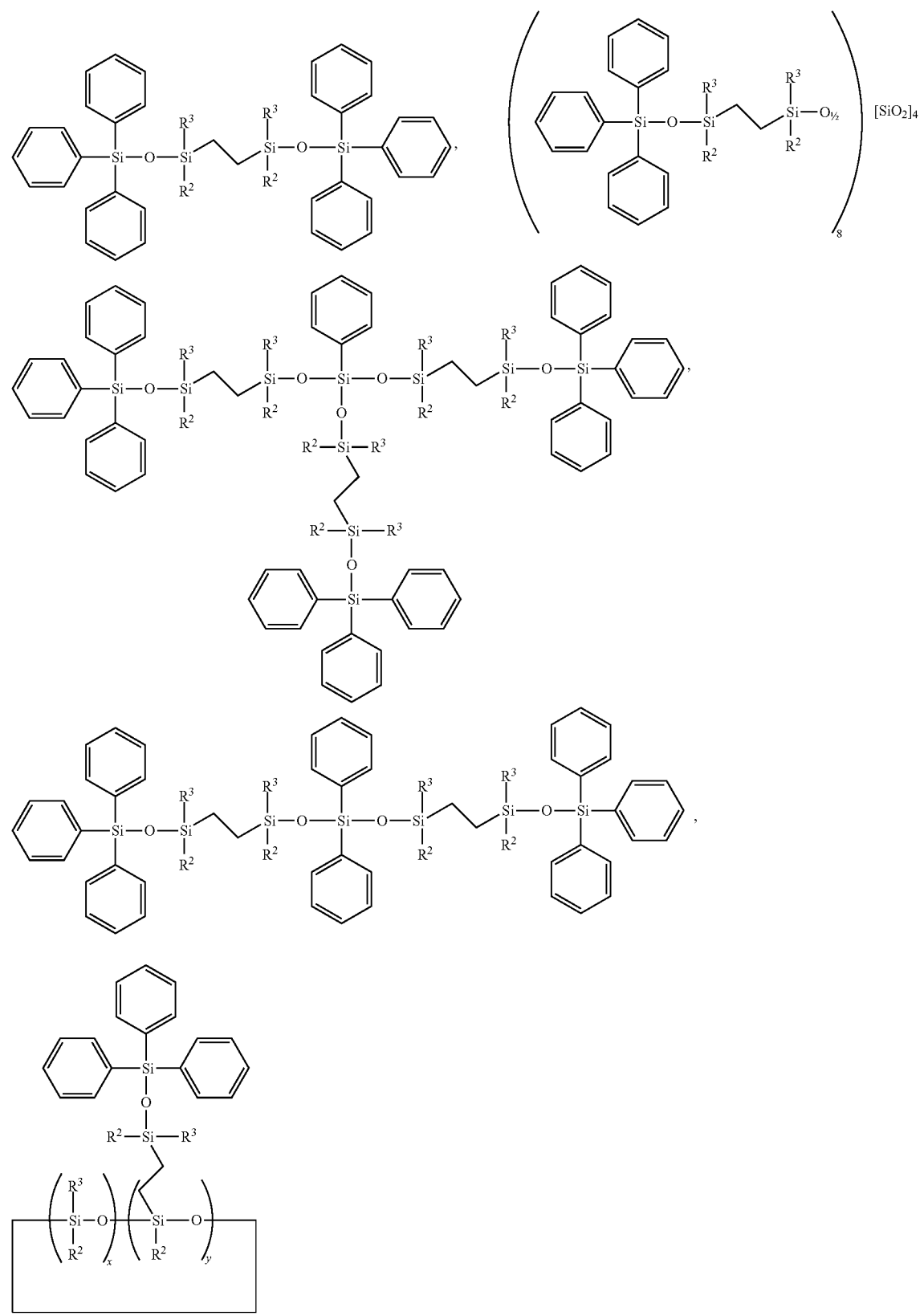
where x is 2 and y is 2.

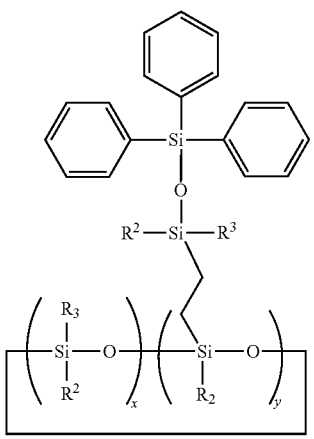

where x is 1 and y is 3, and

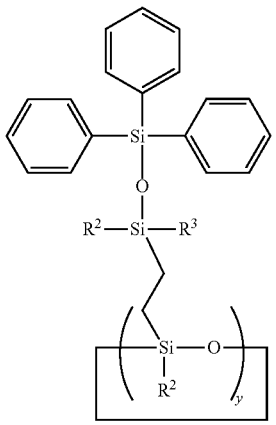

where y is 4,

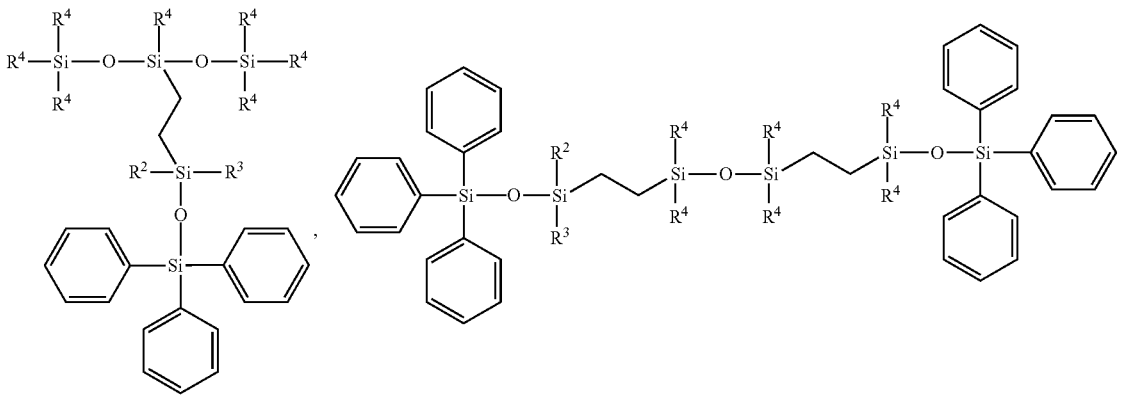

wherein in each of the foregoing formulae $R^2$, $R^3$ and $R^4$ are each independently a monovalent hydrocarbon radical containing up to about 6 carbon atoms.

In one non-limiting embodiment herein each of $R^2$, $R^3$ and $R^4$ as described herein can be methyl.

In one embodiment herein the silicone compound of the general formula (I) herein, as well as the personal care composition described herein can have a refractive index of greater than 1.5, more specifically greater than 1.52, and most specifically greater than 1.53, and such ranges can in one non-limiting embodiment contain an upper limit of 1.8, snore specifically 1.7, and most specifically 1.6.

In one other embodiment herein the silicone compound of the general formula (I) herein, as well as the personal care composition described herein can have a surface tension of greater than 26 dynes/cm, more specifically greater than 27 dynes/cm and most specifically greater than 27.1 dynes/cm.

In one embodiment the personal care composition herein can further comprise a solvent. In one specific embodiment the solvent is selected from silicone oil, organic oil, hydrocarbon, solvent and combinations thereof. Water (or a water equivalent such as a non-aqueous hydroxylic solvent), siloxane, linear or cyclic, or lipophilic fluid (oil swelling agent, oil swellable) may be used as the solvent which may function as a swelling agent. Lipophilic fluids suitable far use as the solvent component of the composition of the present invention are those described herein. In a snore specific embodiment, the solvent component of the composition of the present invention exhibits a viscosity of below about 1,000 cSt, preferably below about 500 cSt, snore preferably below about 250 cSt, and most preferably below 100 cSt, at 25° C.

In one embodiment, the solvent of the present invention can comprise an emollient compound. Suitable emollient compound include any fluid that provides emollient properties, that is, that when applied to skin, tend to remain, on the surface of the skin or in the stratum corneum layer of the skin, to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In one embodiment, the solvent is a hydrocarbon solvent selected from the group consisting of xylene, toluene, cyclohexane, heptane, octane, iso-octane, isododecanol and mixtures thereof.

In another embodiment herein the solvent is a hydrophilic emollient selected from the group consisting of glycerine, sorbitol, aqueous solution of moisturizing additives and combinations thereof.

In another non-limiting embodiment herein, the solvent is a silicone component represented by general formula IV as described herein.

As used herein the term "non-aqueous hydroxylic organic compound" or "non-aqueous hydroxylic solvent" means hydroxyl containing organic compounds exemplified by alcohols, glycols, polyhydric alcohols and polymeric glycols and mixtures thereof that are liquid at room temperature, e.g. about 25° C., and about one atmosphere pressure, and are used interchangeably with the term "solvent" as the same component. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about atmosphere pressure. Preferably the non-aqueous hydroxylic organic solvent is selected from the group consisting of ethylene glycol, ethanol, propyl alcohol, isopropyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Because it is possible to vary the compositional parameters of the silicone composition of the invention in an almost limit less fashion, by varying the compositional parameters of the silicone composition, some compositions herein are both water swellable and oil swellable while others are only water swellable or oil swellable, and some compositions herein will not be swellable with any of the solvents discussed herein, in one embodiment herein the silicone component of the silicone composition can be swollen with the solvent described herein. In one embodiment, the silicone component described herein can be swollen from its original volume to a swollen volume that is a factor of from 1.01 to 5000, more preferably from 2 to 1000, and even more preferably from 5 to 500, times its original volume. The original volume of the silicone component can be determined, for example, by extracting or evaporating all of the solvent component from the silicone composition of the present invention to leave the original volume, that is, the volume of the silicone component in the absence of the fluid.

In a more specific embodiment, the silicone composition, of the present invention comprises, per 100 parts by weight ("pbw") of the silicone component, from 1 pbw to 99.9 pbw, more preferably from 70 pbw to 99.5 pbw, and still-more preferably from 85 pbw to 99 pbw of the solvent.

In another embodiment herein the silicone composition may further comprise a previous metal catalyst which, be present for further reaction or which may be remaining from a previous reaction of providing the silicone component, e.g., such as the reaction of triphenylsilanol with 1,1,3,3-tetralkayl-1,3-dialkenyldisilazane and/or an alkenyldialkylhalosilane such as is described herein, or alternatively the reaction of 1,1,1-triphenyl-3-3-dialkyl-3-dialkyl-3-alkenyl-disiloxane with a hydrogen siloxane such as is described herein.

Many types of precious metal catalysts, e.g., platinum catalysts are known and such platinum catalysts may be used for the hydrosilylation reaction in the present invention. When optical clarity is required the preferred platinum catalysts are those platinum compound catalysts that are soluble in the reaction mixture. The platinum compound can be selected from those having the formula (PtCl$_2$Olefin) and H(PtCl$_3$Olefin) as described in U.S. Pat. No. 3,159,601, hereby incorporated by reference. A further platinum containing material usable in the compositions of the present invention is the cyclopropane complex of platinum chloride described in U.S. Pat. No. 3,159,662 hereby incorporated by reference. Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979).

In one embodiment the precious metal catalysts that may be used herein, are such as the non-limiting examples of rhodium, ruthenium, palladium, osmium, iridium and platinum catalysts and combinations thereof.

In one embodiment herein the platinum catalyst is in a soluble complex form.

In one other embodiment, the platinum catalyst is selected from the group consisting of platinic chloride, chloroplatinic acid, bis(acetylacetonato)platinum, ($\eta^5$-Cyclopentadienyl) trialkylplatinum and combinations thereof.

Persons skilled in the art can easily determine an effective amount of precious metal catalyst. The catalyst can be present in a very wide range, but normally a range of from between 0.1 and 1000 ppm, more specifically from between 1 and 100 ppm. In one embodiment herein the basis amount of the catalyst is based on the amount of silicone component or the amounts of the respective components used to produce the silicone component.

In one embodiment herein, the silicone compositions of the present invention are self-emulsifying.

In another embodiment herein, the silicone composition may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more carrier solvent may be added to the silicone composition prior to the shearing.

In a specific embodiment, the silicone composition of the present invention is a solid, typically having a creamy consistency, wherein the silicone component acts as a means for gelling the fluid to reversibly impart characteristics of a solid, to the fluid. At rest, the silicone composition exhibits the properties of a solid gel material. The silicone composition of the present invention exhibits high stability and resistance to syneresis, that is, the composition exhibits little or no tendency for fluid to flow from the composition and imparts high stability and syneresis resistance to personal care compositions which include the silicone composition as a component. The high stability and syneresis resistance persists with prolonged aging of such silicone composition and personal care compositions. However, solvent may be released from, the silicone composition by subjecting the silicone composition to a shearing force, such as, for example, by rubbing the composition between one's lingers, to provide improved sensory feel characteristic of the fluid component of the silicone material.

In one specific embodiment, the silicone component is insoluble in various fluid components, but that is capable of being swollen by the solvent.

In another specific embodiment, the structure of the silicone component is effective to allow the cross-polymer to be swollen by a low molecular weight silicone fluid, such as, for example, decamethylcyclopentasiloxane, from its original volume to a swollen volume as stated above.

The silicone component of the present invention may be utilized as prepared or as one component in personal care emulsions. As is generally known, emulsions comprise at least two immiscible phases one of which is continuous and the other which is discontinuous. In one embodiment herein, the non-miscible phases (immiscible phases) can be selected from the group consisting of aqueous, non-aqueous, and solid particulates.

Further emulsions may be liquids with varying viscosities or solids. Additionally, the particle size of the emulsions may render them microemulsions, and when sufficiently small, microemulsions may be transparent. Further it is also possible to prepare emulsions of emulsions and these are generally known as multiple emulsions. These emulsions may be: 1) aqueous emulsions where the discontinuous, phase comprises water and the continuous phase comprises the silicone component of the present invention; 2) aqueous emulsions where the discontinuous phase comprises the silicone component of the present invention and the continuous phase comprises water; 3) non-aqueous emulsions where the discontinuous phase comprises a non-aqueous hydroxylic solvent and the continuous phase comprises the silicone component of the present invention; and 4) non-aqueous emulsions where the continuous phase comprises a non-aqueous hydroxylic organic solvent and the discontinuous phase comprises the silicone component of the present invention.

In one embodiment herein, the silicone component is compatible with a particulate additive. In another more specific embodiment, the particulate additive is selected from inorganic particulates, polymeric latexes, and pigments.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into personal care formulations for hair care, skin care, and the like. In one embodiment herein, the crosslinked ionic silicone network can bind and slow release cosmetic actives.

In one embodiment herein there is provided a personal care application comprising the silicone composition described herein. Some non-limiting examples of personal care applications can comprise skin care products, sun care products, color cosmetic products, hair care products and luster enhancers.

In one more specific embodiment herein the personal care formulation can be a personal care application selected from die group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish with and without pigments, nail polish remover, nail creams and lotions, cuticle softeners, protective creams such as sunscreen, insect repellent and anti-aging products, color cosmetics such as lipsticks, lip-glosses, lip balms, foundations, face powders, eye liners, eye shadows, blushes, makeup, mascaras, BB creams, CC creams and other personal care formulations where silicone components have been conventionally added, as well as drug delivery systems for topical application of medicinal compositions that are to be applied to the skin.

In a more specific embodiment, personal care composition comprises one or more silicone components of the present invention and further comprises one or mom following optional ingredients.

Fatty Substances

The fatty substances may contain independently or in combination, oils and waxes. The term oil means a compound that is liquid at room temperature. The term wax means a compound that is solid or substantially solid at room temperature and whose melting point is generally greater than 35° C.

Examples of oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat, germ oil, corn oil, sunflower oil, karite butter, castor oil, sweet almond oil, macadamia oil, apricot oil, soybean oil, rapeseed oil, cottonseed oil, coconut oil, argan oil, jojoba oil, shea butter, cocoa butter, macadamia oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including and better still from 7 to 19 carbon atoms, and $R_6$ represents a branched hydrocarbon-based chairs containing from 1 to 40 carbon atoms, including and better still from 3 to 20 carbon atoms, with $R_5+R_6 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Examples of tatty substances which can be used in the compositions of the present invention include non polar compounds such as; hydrocarbons, mineral oil, polyolefins such as polydecene, paraffins such as isohexadecane (e.g. Permethyl 99® and Permethyl 101®, isododecane, isodecane, petrolatum, high molecular weight, polybutenes.

Waxy compounds that are exemplary include carnauba wax, beeswax, ozokerite wax, candelilla wax, hydrogenated castor oil, polyethylene waxes and polymethylene waxes, for instance the product marketed under the trademark Cirebelle 303 by Sasol.

Organic Sunscreens

The organic screening agents are selected especially from among anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives.

Examples of additional organic photoprotective agents include those indicated herein below under their INCI name:

Cinnamic Derivatives: Ethylhexyl methoxycinnamate marketed in particular under the trademark Parsol MCX by DSM Nutritional Products, Inc., Isopropyl methoxycinnamate, Isoamyl methoxycinnamate marketed under the trademark Neo Heliopan E 1000 by Symrise, Cinoxate, DEA methoxycinnamate, Diisopropyl methylcinnamate, Glyceryl ethylhexanoate dimethoxycinnamate.

Para-Aminobenzoic Acid Derivatives:

PABA, Ethyl PABA, Ethyl dihydroxypropyl PABA, Ethylhexyl dimethyl PABA marketed in particular under the trademark Escalol 507 by ISP, Glyceryl PABA, PEG-25 PABA marketed under the trademark Uvinul P25 by BASF.

Salicylic Derivatives:

Homosalate marketed under the trademark Eusolex HMS by Rona/EM industries, Ethylhexyl salicylate marketed under the trademark Neo Heliopan OS by Symrise, Dipropylene glycol salicylate marketed under the trademark Dipsal by Scher, TEA salicylate marketed under the trademark Neo Heliopan TS by Symrise.

β,β-Diphenylacrylate Derivatives;

Octocrylene marketed in particular under the trademark Uvinul N539 by BASF, Etocrylene marketed in particular under the trademark Uvinul N35 by BASF.

Benzophenone Derivatives:

Benzophenone-1 marketed under the trademark Uvinul 400 by BASF. Benzophenone-2 marketed under the trademark Uvinul D50 by BASF, Benzophenone-3 or Oxybenzone marketed under the trademark Uvinul M40 by BASF, Benzophenone-4 marketed under the trademark Uvinul MS40 by BASF, Benzophenone-5, Benzophenone-6 marketed under the trademark Helisorb 11 by Norquay, Benzophenone-8 marketed under the trademark Spectra-Sorb UV-24 by American Cyanamid, Benzophenone-9 marketed under the trademark Uvinul DS-49 by BASF, Benzophenone-12 n-hexyl 2-(4-diethylamino-2-hydroxybenzoyl)benzoate marketed under the trademark Uvinul A+ by BASF.

Benzylidenecamphor Derivatives:

3-Benzylidenecamphor manufactured under the trademark Mexoryl SD by Chimex, 4-Methylbenzylidenecamphor marketed under the trademark Eusolex 6300 by Merck, Benzylidenecamphorsulfonic acid manufactured under the trademark Mexoryl SL by Chimex, Camphor benzalkonium methosulfate manufactured under the trademark Mexoryl SO by Chimex, Terephthalylidenedicamphorsulfonic acid manufactured under the trademark Mexoryl SX by Chimex, Polyacrylamidomethylbenzylidenecamphor manufactured under the trademark Mexoryl SW by Chimex.

Phenylbenzimidazole Derivatives:

Phenylbenzimidazolesulfonic acid marketed in particular under the trademark Eusolex 232 by Merck. Disodium phenyl dibenzimidazole tetrasulfonate marketed under the trademark Neo Heliopan AP by Symrise.

Phenylbenzotriazole Derivatives:

Drometrizole trisiloxane marketed under the trademark Silatrizole by Rhodia Chimie, Methylenebis(benzotriazolyl) tetramethylbutylphenol marketed in solid form under the trademark MIXXIM BB/100 by Fairmount Chemical, or in micronized form as an aqueous dispersion under the trademark Tinosorb M by Ciba Specialty Chemicals.

Triazine Derivatives:

Bis(ethylhexyloxyphenol)methoxyphenyltriazine marketed under the trademark Tinosorb S by Ciba Geigy, Ethylhexyltriazone marketed in particular under the trademark Uvinul T150 by BASF, Diethylhexylbutamidotriazone marketed under the trademark Uvasorb HEB by Sigma 3V, 2,4-bis(n-butyl 4'-aminobenzoate)-6-(aminopropyltrisiloxane)-s-triazine, 2,4,6-tris(dineopentyl 4'-aminobenzalmalonate)-s-triazine 2,4,6-tris(diisobutyl 4'-aminobenzalmalonate)-s-triazine, 1a 2,4bis(4'-aminobenzoate de n-butyle)-6-(aminopropyltrisiloxane)-s-triazine, 2,4-bis(dineopentyl 4'-aminobenzalmalonate)-6-(n-butyl 4'-aminobenzoate)-s-triazine, the symmetrical triazine screening agents described in U.S. Pat. No. 6,225,467, WO 2004/085 412 (see compounds 6 and 9) or the document Symmetrical Triazine Derivatives IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in WO 06/035 000, WO 06/034 982, WO 06/034 991, WO 06/035 007, WO 2006/034 992 and WO 2006/034 985.

Anthranilic Derivatives:

Menthyl anthranilate marketed under the trademark Neo Heliopan MA by Symrise.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, marketed under the trademark Parsol SLX by DSM Nutritional products, Inc.

4,4-Diarylbutadiene Derivatives:

1,1-Dicarboxy(2,2'-dimethylpropyl)-4,4-diphenylbutadiene.

Benzoxazole Derivatives:

2,4-bis[5-(1-dimethylpropyl)benzoxazole-2-yl(4-phenyl) imino]-6-(2-ethylhexyl)imino-1,3,5-triazine marketed under the trademark Uvasorb K2A by Sigma 3V.

Merocyanin Derivatives:

Octyl 5-N,N-diethylamino-2-phenylsulfonyl-2,4-pentadienoate, and mixtures thereof.

The Preferred Organic Photoprotective Agents are Selected from Among:

Ethylhexyl methoxycinnamate, Ethylhexyl salicylate, Homosalate, Octocrylene, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Bis(ethylhexyloxyphenol)methoxyphenyltriazine, Ethylhexyltriazone, Diethylhexylbutamidotriazone, 2,4-bis (4'-aminobenzoate of n-butyl)-6-(aminopropyltrisiloxane)-s-triazine, 2,4,6-Tris(dineopentyl 4'-aminobenzalmalonate)-s-triazine, 2,4,6-Tris(diisobutyl 4'-aminobenzalmalonate)-s-triazine, 2,4-Bis(dineopentyl 4'-aminobenzalmalonate)-6-(n-butyl 4'-aminobenzoate)-s-triazine, 2,4,6-Tris (terphenyl)-1,3,5-triazine, Drometrizole trisiloxane, Polysilicone-15, 1,1-Dicarboxy(2,2'-dimethylpropyl)-4,4-diphenylbutadiene, 2,4-Bis[5-1(dimethylpropyl)benzoxazol-2-yl(4-phenyl)imino]-6-(2-ethylhexyl)imino-1,3,5-triazine, Octyl 5-N,N-diethylamino-2-phenylsulfonyl-2,4-pentadienoate, and mixtures thereof.

Humectants

Suitable humectants include, but are not limited to polyhydric alcohols (polyols). Examples of polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the polyhydric alcohol is glycerin.

Other humectants or moisturizers include urea and derivatives thereof, especially Hydrovance® marketed by National Starch, lactic acid, hyaluronic acid, AHAs, BHAs, sodium pidolate, xylitol serine, sodium lactate, ectoin and derivatives thereof, chitosan and derivatives thereof, collagen, plankton, an extract of Imperata cylindra marketed under the trademark Moist 24® by Sederma, acrylic acid homopolymers, for instance Lipidure-HM® from NOF Corporation, beta-glucan from Mibelle-AG-Biochemistry; a mixture of passionflower oil, apricot oil, corn oil and rice bran oil marketed by Nestle under the trademark. NutraLipids®; a C-glycoside derivative such as those described in WO 02/051 828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an oil of the microalga Prophyridium cruentum enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon; and arginine.

Suitable moisturizers can also include sodium PCA and amino acid derived moisturizers, for examples the ingredients under the trademarks Prodew 500, Ajldew NL-50.

Silicones

The silicones can be linear polydimethylsiloxane polymers, dimethiconol polymers, alkyl silicones, silicone quats, phenyl modified silicones, aminofunctional silicones, aminofunctional silicones emulsions, silicone gum, silicone crosspolymer network, silicone resins (T resin or Q resin) Silicone waxes. Examples of silicone polymers include the polymers from Momentive: aminosilicones under the tradename Silsoft AX, Silsoft AX-E, SF1708, Silsoft A+, silicone waxes under the tradename SF1632, SF1642, the silicone resins under the trademarks Silform Flexible, SR1000, SS4230, SS4267, Silform FR-5, Silform FR-10, Silsoft Style, the silicone gels under the trademarks Velvesil 034, Velvesil FX, Velvesil Plus, Velvesil DM, Silsoft silicone gel, SFE839, the silicone gums under the trademark Silsoft1215, SF1236, CF1251, the silicone quats under the trademarks, silsoft Q, Silsoft Silk, the alkyl silicone under the trademark Silsoft ETS, Silsoft 034.

Silicone elastomers useful in accordance with the invention include, without limitation, compounds generally known as polyorganosiloxanes.

The elastomers are by definition crosslinked, the degree of which can be vary depending on the elastic properties of the polymer that are desired. Cross-linking materials may be hydrophilic (ethylene oxide and propylene oxide, for example), hydrophobic (dimethicone, vinyl dimethicone, alkyl, etc.) or combinations thereof.

The silicone elastomers are typically dissolved in a suitable solvent, either prior to their introduction into the composition of the invention, or in situ within the composition. Examples of suitable solvents, include, but are not limited to, volatile and non-volatile silicones, volatile and non-volatile alcohols, volatile and non-volatile esters, volatile and non-volatile hydrocarbons and mixtures thereof. Preferred silicone elastomers for use herein are elastomer/solvent blends, also referred to as "gels", having an elastomer to solvent ratio of from about 1:100 to about 1:1, more preferably from about 1:50 to about 1:5. Preferably the silicone elastomer/solvent blend has a viscosity of no more than 7,500,000 centipoise, more preferably no more than 500,000 centipoise. Preferably the silicone elastomer blend has a viscosity of at least than 1,000 centipoise, more preferably at least 10,000 centipoise.

Other examples of silicones include silicone elastomers such as KSG6 (Shin-Etsu), Trefil E-505C or Trefil E-506C, now known as DC 9506 (dimethicone/vinyldimethicone crosspolymer, Dow-Corning and Toray), Gransil SR-CYC, SR DMF10, SR-DC556 (Grant Industries), KSP 100 and 200 series and KMP series (Shin Etsu), KSG15, KSG17, KSG16, and KSG18 (Shin-Etsu), Gransil SR 5CYC gel Gransil SR DMF 10 gel, Gransil SR DC556 gel, SF 1204 and JK 113 (General Electric), DC 9040 (cyclomethicone and dimethicone crosspolymer blend, Dow Corning), DC 9701 (dimethicone/vinyl dimethicone cross-polymer coated with silica, Dow Corning). A mixture of these commercial products may also be used.

Solid Particles

Suitable solid particles include, but are not limited to ingredients which may be compounded in the composition of the present invention include inorganic powder such as gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as ethylene acrylate, latex, polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Preferred organic powders/fillers include, but are not limited, to polymeric particles chosen from the methylsilsesqiuoxane resin microspheres such as for example those sold by Toshiba silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat CO5, polystyerene microspheres such as for example those sold by Dyno Particles under the name Dynospheres, ethylene acrylate copolymer sold by Koho under the name FloBead EA209 and mixtures thereof.

Also useful herein are pigment and/or dye encapsulates such nanocolorants from BASF and multi-layer interference pigments such as Sicopearls from BASF.

Mixtures of the above powders may also be used.

The particulates can be selected from among a rice starch or a corn starch, kaolinite, talc, a pumpkin seed extract, cellulose microbeads, plant fibers, synthetic fibers, in particular polyamide fibers, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of additional particles may especially be mentioned include: rice or corn starch, in particular an aluminum starch octenyl succinate marketed under the trademark Dry Flo® by National Starch; kaolinite; silicas; talc; a pumpkin seed extract, as marketed under the trademark Curbilene® by Indena; cellulose microbeads; fibers, such as silk fiber, cotton fiber, wool fiber, flax fiber, cellulose fiber extracted especially from wood, from vegetables or from algae, polyamide fiber (Nylon®), modified cellulose fiber, poly-p-phenyleneterephthamide fiber, acrylic fiber, polyolefin fiber, glass fiber, silica fiber, aramid fiber, carbon, fiber, Teflon® fiber, insoluble collagen fiber, polyester fiber, polyvinyl chloride or polyvinylidene chloride fiber, polyvinyl alcohol fiber, polyacrylonitrile fiber, chitosan fiber, polyurethane fiber, polyethylene phthalate fiber, fibers formed from a mixture of polymers, resorbable synthetic fibers, expanded acrylic copolymer microspheres such as those marketed by EXPANCEL under the trademark Expancel 551®;

Fillers with an optical effect, in particular; polyamide powders (Nylon®), for instance Nylon 12 particles of the Orgasol type from Arkema, with a mean size of 10 microns and a refractive index of 1.54, silica powders, for instance Silica beads SB150 from Miyoshi with a mean size of 5 microns and a refractive index of 1.45, polytetrafluoroethylene powders, for instance PTFE Ceridust 9205F from Clariant, with a mean size of 8 microns and a refractive index of 1.36, silicone resin powders, for instance the silicone resin with trademarks Tospearl 150KA, Tospearl 1110A, Tospearl 120A, Tospearl 145A, Tospearl 2000B, Tospearl 3000A from Momentive, acrylic copolymer powders, especially of polymethyl(meth)acrylate, for instance the PMMA particles Jurymer MBI from Nihon Junyoki, or the Micropearl M100® and F 80 ED® particles from the company Matsumoto Yushi-Seiyaku, wax powders, for instance the paraffin wax particles Microease 114S from Micropowders, polyethylene powders, especially comprising at least, one ethylene/acrylic acid copolymer, and in particular consisting of ethylene/acrylic acid copolymers, for instance the particles Flobeads EA 209 from Sumitomo, elastomeric crosslinked organopolysiloxane powders coated with, silicone resin, especially with silsesquioxane resin. Such elastomeric powders are marketed under the trademarks KSP-100, KSP-101, KSP-102, KSP-103, KSP-104 and KSP-105 by Shin-Etsu, and talc/titanium dioxide/alumina/silica composite powders such as those marketed under the trademark Coverleaf® AR-80 by Catalyst & Chemicals, mixtures thereof, compounds that absorb and/or adsorb sebum.

Mention may be made especially of: silica powders, for instance the porous silica microspheres marketed under the trademark Silica Beads SB-700 marketed by Miyoshi, the products Sunsphere® H51, Sunsphere® H33 and Sunsphere® H53 marketed by Asahi Glass; the polydimethylsiloxane-coated amorphous silica microspheres marketed under the trademark SA Sunsphere® H-33 and SA Sunsphere® H-53 marketed by Asahi Glass; amorphous mixed silicate powders, especially of aluminum and magnesium, for instance the product marketed under the trademark Neusilin UFL2 by Sumitomo; polyamide (Nylon®) powders, for instance Orgasol® 4000 marketed by Arkema, and acrylic polymer powders, especially of polymethyl methacrylate, for instance Covabead® LH85 marketed by Wacker; of polymethyl methacrylate/ethylene glycol dimethacrylate, for instance Dow Corning 5640 Microsponge® Skin Oil Adsorber marketed by Dow Corning, or Ganzpearl® GMP-0820 marketed by Ganz Chemical; of polyallyl methacrylate/ethylene glycol dimethacrylate, for instance Poly-Pore® L200 or Poly-Pore® E200 marketed by Amcol; of ethylene glycol dimethacrylate/lauryl methacrylate copolymer, for instance Polytrap® 6603 marketed by Dow Corning;

Silicate particles, such as alumina silicate;

Mixed silicate particles, such as: magnesium aluminum silicate particles, such as saponite or hydrated magnesium aluminum silicate with a sodium sulfate marketed under the trademark Sumectone® by Kunimine; the magnesium silicate, hydroxyethylcellulose, black cumin oil, marrow oil and phospholipids complex or Matipure® from Lucas Meyer, and mixtures thereof. Other examples of matting agents are boron nitride particles, such as Softtouch CCS402, Softtouch CC6097, Softtouch CC6064. Suitable solid particles are fillers with a Soft-Focus Effect. These fillers may be any material capable of modifying and hiding wrinkles by virtue of their intrinsic physical properties.

These fillers may especially modify wrinkles via a tensioning effect, a covering effect or a soft-focus effect. Examples of such fillers include the following compounds: porous silica microparticles, for instance the Silica Beads® SB150 and SB700 from Miyoshi with a mean size of 5 μm; the series-H Sunspheres® from Asahi Glass, hollow hemispherical silicone resin particles such as NLK 500®, NLK 506® and NLK 510® from Takemoto Oil and Fat; silicone resin powders, for instance the silicone resin Tospearl® 145A from Momentive; acrylic copolymer powders, especially of polymethyl (meth)acrylate, for instance the PMMA particles Jurymer MBI® from Nihon Junyoki, with a mean size of 8 μm, the hollow PMMA spheres marketed under the trademark Covabead® LH85 by Wacker, and vinylidene/acrylonitrile/methyl methacrylate expanded microspheres marketed under the trademark Expancel®; wax powders, for instance the paraffin wax particles MicroEase® 114S from MicroPowders, with a mean size of 7 μm; polyethylene powders, especially comprising at least one ethylene/acrylic acid copolymer, and in particular consisting of ethylene/acrylic acid copolymers, for instance the Flobeads® EA 209 particles from Sumitomo, with a mean size of 10 μm; crosslinked elastomeric organopolysiloxane powders coated with silicone resin and especially with silsesquioxane resin, under the trademarks KSP-100®, KSP-101®, KSP-102®. KSP-103®, KSP-104® and KSP-105® by Shin-Etsu; talc/titanium dioxide/alumina/silica composite powders, for instance those marketed under the trademark Coverleaf AR-80® by Catalyst & Chemicals: talc, mica, kaolin, lauryl glycine, starch powders crosslinked with octenyl succinate anhydride, boron nitride, polytetrafluoroethylene powders, precipitated calcium carbonate, magnesium carbonate, magnesium hydrogen carbonate, barium sulfate, hydroxyapatite, calcium silicate, cerium dioxide and glass or ceramic microcapsules; hydrophilic or hydrophobic, synthetic or unnatural, mineral or organic fillers such as silk fibers, cotton fibers, wool fibers, flax fibers, cellulose fibers extracted especially from wood, vegetables or algae, Polyamides (Nylon®) fibers, modified cellulose fibers, poly-p-terephthamide fibers, acrylic fibers, polyolefin fibers, glass fibers, silica fibers, aramid fibers, carbon fibers, polytetrafluoroethylene (Teflon®) fibers, insoluble collagen fibers, polyester fibers, polyvinyl chloride fibers, polyvinylidene chloride fibers, polyvinyl alcohol fibers, polyacrylonitriles fibers, chitosan fibers, polyurethane fibers, polyethylene phthalate fibers, fibers formed from a mixture of polymers, resorbable synthetic fibers, spherical elastomeric cross-linked silicones, for instance Trefil E-505C® or E-506C® from Dow Corning; abrasive fillers, which, via a mechanical effect, smooth out the skin microrelief, such as abrasive silica, for instance Abrasif SF® from Semanez or nutshell powders (for example of apricot or walnut, from Cosmetochem).

The fillers with an effect on the signs of aging are especially selected from among porous silica microparticles, hollow hemispherical silicones. Silicone resin powders, acrylic copolymer powders, polyethylene powders, crosslinked elastomeric organopolysiloxane powders coated with silicone-resin, talc/titanium dioxide/alumina/silica composite powders, precipitated calcium carbonate, magnesium carbonate, magnesium hydrogen carbonate, barium sulfate, hydroxyapatite, calcium silicate, cerium dioxide, glass or ceramic microcapsules, and silk fibers or cotton fibers, and mixtures thereof.

The filler may be a soft-focus filler. The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical. The soft-focus fillers may be selected from among silica and silicate powders, especially alumina powder, powders of polymethyl methacrylate (PMMA) type, talc, silica/TiO2 or silica/zinc oxide composites, polyethylene powders, starch powders, polyamide powders, styrene/acrylic copolymer powders and silicone elastomers, and mixtures thereof. Mention may be made in particular of talc with a number-average size of less than or equal to 3 microns, for example talc with a number-average size of 1.8 microns and especially the product marketed under the trademark Talc P3® by Nippon Talc, Nylon® 12 powder, especially the product marketed under the trademark Orgasol 2002 Extra D Nat Cos® by Atochem, silica particles 1% to 2% surface-treated with a mineral wax (INCI name; hydrated silica (and) paraffin) such as the products marketed by Degussa, amorphous silica microspheres, such as the products marketed under the trademark Sunsphere, for example of reference H-53® by Asahi Glass, and silica microbeads such as those marketed under the trademark SB-700® or SB-150® by Miyoshi, this list not being limiting.

The particles may include pearlescent pigments such as, for example, bismuth oxychloride and titanium dioxide coated mica.

Inorganic Sunscreens

The additional mineral screening agents are selected from among coated or uncoated metal oxide pigments in which the mean size of the primary particles is preferentially from 5 nm to 100 nm (preferably from 10 nm to 50 nm), for instance titanium oxide (amorphous or crystallised in rutile and/or anatase form), iron oxide, zinc oxide, zirconium oxide or cerium oxide pigments, which are all UV-photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkyl silanes.

The silicones used for coating the nanopigments that are suitable for the present invention are preferably selected from among the group containing alkyl silanes, polydialkylsiloxanes and polyalkylhydrogenosiloxanes. Even more preferentially, the silicones are selected from among the group containing octyltrimethylsilane, polydimethylsiloxanes and polymethylhydrogenosiloxanes.

Before being treated with silicones, the metal oxide pigments may have been treated with other surface agents, in particular with cerium oxide, alumina, silica, aluminum compounds or silicon compounds, or mixtures thereof.

The coated pigments are more particularly titanium oxides that have been coated: with silica, such as the product Sunveil from the company Ikeda and the product Eusolex T-AVO from the company Merck, with silica and iron oxide, such as the product Sunveil F from the company Ikeda, with silica and alumina, such as the products Microtitanium Dioxide MT 500 SA and Microtitanium Dioxide MT 100 SA from the company Tayca, Tioveil from the company Tioxide and Mirasun TiW 60 from the company Rhodia, with alumina, such as the products Tipaque TTO-55 (B) and Tipaque TTO-55 (A) from the company Ishihara and UVT 14/4 from the company Kemira, with alumina and aluminum stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Uniqema, with silica, alumina and alginic acid, such as the product MT-100 AQ from the company Tayca, with alumina and aluminum laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR351 tram the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminum stearate and treated with a silicone, such as the product STT-30-DS from the company Titan Kogyo, with silica and treated with a silicone, such as the product UV-Titan X 195 from the company Kemira, or the product SMT-100 WRS from the company Tayca, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

Other titanium oxide pigments treated with a silicone are preferably TiO2 treated with octyltrimethylsilane and for which the mean size of the elementary particles ranges from 25 to 40 nm, such as the product marketed under the trademark T 805 by Degussa Silices, TiO2 treated with a polydimethylsiloxane and for which the mean size of the elementary particles is 21 nm, such as the product marketed under the trademark 70250 Cardre UF TiO2SI3 by Cardre, anatase/rutile TiO2 treated with a polydimethylhydrogenosiloxane and for which the mean size of the elementary particles is 25 nm, such as the product marketed under the trademark Microtitanium Dioxide USP Grade Hydrophobic by Color Techniques.

The uncoated titanium oxide pigments are marketed, for example, by Tayca under the trademarks Microtitanium Dioxide MT 500 B or Microtitanium Dioxide MT 600 B, by Degussa under the trademark P 25, by Wacker under the trademark Transparent titanium oxide PW, by Miyoshi Kasei under the trademark UFTR, by Tomen under the trademark ITS and by Tioxide under the trademark Tioveil AQ.

The uncoated zinc oxide pigments are, for example; those marketed under the trademark Z-Cote by Sunsmart; those marketed under the trademark Nanox by Elementis; those marketed under the trademark Nanogard WCD 2025 by Nanophase Technologies.

The coated zinc oxide pigments are, for example: those marketed under the trademark Z-Cote HP1 by Sunsmart (dimethicone-coated ZnO); those marketed under the trademark Zinc Oxide CS-5 by Toshibi (ZnO coated with polymethylhydrogenosiloxane); those marketed under the trademark Nanogard Zinc Oxide FN by Nanophase Technologies (as a 40% dispersion, in Finsolv TN, C12-C15 alkyl benzoate); those marketed under the trademark Daitopersion ZN-30 and Daitopersion ZN-50 by Daito (dispersions in cyclopolymethylsiloxane/oxyethylenated polydimethylsiloxane, containing 30% or 50% of nanozinc oxides coated with silica and polymethylhydrogenosiloxane); those marketed under the trademark NFD Ultrafine ZnO by Daikin (ZnO coated with perfluoroalkyl phosphate and copolymer based on perfluoroalkylethyl as a dispersion in cyclopentasiloxane); those marketed under the trademark SPD-Z1 by Shin-Etsu (ZnO coated with silicone-grafted acrylic polymer, dispersed in cyclodimethylsiloxane); those marketed under the trademark Escalol Z100 by ISP (alumina-treated ZnO dispersed in an ethylhexyl methoxycinnamate/PVP-hexadecene/methicone copolymer mixture); those marketed under the trademark Fuji ZnO-SMS-10 by Fuji Pigment (ZnO coated with silica and polymethylsilsesquioxane); those marketed under the trademark Nanox Gel TN by Elementis (ZnO dispersed at a concentration of 55% in C12-C15 alkyl benzoate with hydroxystearic acid polycondensate).

The uncoated cerium oxide pigments are marketed under the trademark Colloidal Cerium Oxide by Rhone-Poulene. The uncoated iron oxide nanopigments are marketed, for example, by Arnaud under the trademarks Nanogard WCD 2002 (FE 45B), Nanogard Iron FE 45 BL AQ, Nanogard FE 45R AQ and Nanogard WCD 2006 (EE 45R) or by Mitsubishi under the trademark TY-220. The coated iron oxide pigments are marketed, for example, by Arnaud under the trademarks Nanogard WCD 2008 (FE 45B FN), Nanogard WCD 2009 (FE 45B 556), Nanogard FE 45 BF 345 and Nanogard FE 45 BL or by BASE under the trademark Transparent Iron Oxide. Also exemplary are mixtures of metal oxides, especially of titanium dioxide and of cerium dioxide, including the silica-coated equal-weight mixture of titanium dioxide and of cerium dioxide, marketed by Ikeda under the trademark Sunveil A, and also the alumina, silica, and silicone-coated mixture of titanium dioxide and of zinc dioxide, such as the product M 261 marketed by Kemira, or the alumina, silica and glycerol-coated mixture of titanium dioxide and of zinc dioxide, such as the product M 211 marketed by Kemira.

The additional UV-screening agents are generally present in the compositions according to the invention in proportions ranging from 0.01% to 20% by weight relative to the total weight of the composition, and preferably ranging front 0.1% to 10% by weight relative to the total weight of the composition.

Organic Solvents

Among the organic solvents that are exemplary are lower alcohols and polyols. These polyols may be selected from among glycols and glycol ethers, for instance ethylene glycol, propylene glycol, butylene glycol, dipropylene glycol or diethylene glycol.

Thickeners

Hydrophilic thickeners that are exemplary include carboxyvinyl polymers such as the Carbopol products (carbomers) and the Pemulen products (acrylate/C10-C30-alkylacrylate copolymer); polyacrylamides, for instance the crosslinked copolymers marketed under the trademarks Sepigel 305 (CTFA name: polyacrylamide/C13-C14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methlylpropanesulfonic acid) marketed by Hoechst under the trademark Hostacerin AMPS (CTFA name: ammonium polyacryloyldimethyltaurate) or Simulgel 800 marketed by SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; and mixtures thereof.

Lipophilic thickeners that are exemplary include synthetic polymers such as poly(C10-C30 alkyl acrylates) marketed under the trademark Intelimer IPA 13-1 and Intelimer IPA 13-6 by Landec, or modified clays such as hectorite and its derivatives, for instance the products marketed under the trademark Bentone.

The compositions according to the invention may be formulated according to techniques that are well known to one skilled in this art. They may be in particular in the form of a simple or complex emulsion (O/W, W/O, O/W/O or W/O/W emulsion) such as a cream, a milk or a cream-gel; in the form of an aqueous gel; in the form of a lotion. They may optionally be packaged as an aerosol and may be in the form of a mouse or a spray.

The compositions according to the invention are preferably in the form of an oil-in-water or water-in-oil emulsion.

Emulsifiers

The emulsions can contain emulsifiers selected from among amphoteric, anionic, cationic and nonionic emulsifiers, which are used alone or as a mixture. The emulsifiers are appropriately selected according to the emulsion to be obtained (W/O or O/W). The emulsions may also contain stabilizers of other types, for instance fillers, gelling polymers or thickeners.

As emulsifying surfactants that may be used for the preparation of the W/O emulsions, examples include sorbitan, glycerol or sugar alkyl esters or ethers; silicone surfactants, for instance dimethicone copolyols, such as the mixture of cyclomethicone and of dimethicone copolyol, marketed under the trademark DC 5225 C by Dow Corning, and alkyldimethicone copolyols such as laurylmethicone copolyol marketed under the trademark Dow Corning 5200 Formulation Aid by Dow Corning; cetyldimethicone copolyol, such as the product marketed under the trademark Abil EM 90R by Goldschmidt, and the mixture of cetyldimethicone copolyol, of polyglyceryl isostearate (4 mol) and of hexyl laurate, marketed under the trademark Abil WE O9 by Goldschmidt. Other examples are the silicone emulsifiers from Momentive under the trademarks SF1528, SF1540, Silform EOF, Silform 60-A.

One or more co-emulsifiers may also be added thereto, which may be selected advantageously from the group comprising polyol alkyl esters.

Polyol alkyl esters that are especially exemplary include polyethylene glycol esters, for instance PEG-30 dipolyhydroxystearate, such as the product marketed under the trademark Arlacel P135 by ICI.

Glycerol and/or sorbitan esters that are especially exemplary include, for example, polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

For the O/W emulsions, examples of emulsifiers include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate marketed, for example, by ICI under the trademark Arlacel 165; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the trademark Montanov 68 by SEPPIC, under the trademark Tegocare CG90 by Goldschmidt and under the trademark Emulgade KE3302 by Henkel, and also arachidyl glucoside, for example in the form of a mixture of arachidyl alcohol, behenyl alcohol and arachidyl glucoside, marketed under the trademark Montanov 202 by SEPPIC. Examples of silicones emulsifiers, suitable for O/W emulsions are the polyether siloxane copolymers under the trademarks, SF1188A, SF1288, Silsoft 880, Silsoft 860, Silsoft 440, Silsoft 895, Silsoft 900.

Among the other emulsion stabilizers that will be used more particularly are isophthalic acid or sulfoisophthalic acid polymers, and in particular phthalate/sulfoisophthalate/glycol copolymers, for example the diethylene glycol/phthalate/isophthalate/1,4-cyclohexanedimethanol copolymer (INCI name: Polyester-5) marketed under the trademark Eastman AQ Polymer (AQ65S, AQ38S, AQ55S and AQ48 Ultra) by Eastman Chemical.

Other suitable emulsifiers are the amino-based emulsifiers, such as sodium stearoyl glutamate and phospholipids such as lecithin, hydroxylated lecithin Film-Forming Polymer According to preferred embodiments of the present invention, the compositions may comprise at least one film-forming polymer.

In the present invention, the term "film-forming polymer" means a polymer that is capable, by itself or in the presence of an auxiliary film-forming agent, of forming a macroscopically continuous deposit on keratin materials. The composition may comprise an aqueous phase, and the film-forming polymer may be present in this aqueous phase. In this case, it will preferably be a polymer in dispersion or an amphiphilic or associative polymer.

The term polymer in dispersion" means water-insoluble polymers present in the form of particles of variable size. The polymer may or may not be crosslinked. The size of the polymer panicles is typically between 25 and 500 nanometers and preferably between 50 and 200 nanometers. The following polymers in aqueous dispersion may be used: Ultrasol 2075 from Ganz Chemical, Daitosol 5000 AD from Daito Kasei, Avalure UR 450 from Noveon, Dynam X from National Starch, Syntran 5760 from Interpolymer, Aeusol OP 301 from Roehm & Haas, and Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo: Syntran 5760® by the company Interpolymer, Soltex OPT by the company Roehm & Haas, aqueous dispersions of acrylic or styrene/acrylic polymers sold under the brand name Joncryl® by the company Johnson polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX 1100 from Elementis, Aculyn 22, Aculyn 44 and Aculyn 46 from Roehm & Haas, Viscophobe DB 1000 from Amerchol. Diblock copolymers formed from a hydrophilic block (polyacrylate or polyethylene glycol) and from a hydrophobic block (polystyrene or polysiloxane) may also be used.

The composition may comprise an oily phase and the film-forming polymer may be present in this oily phase. The polymer may then be in dispersion or in solution.

As examples of lipodispersible non-aqueous film-forming polymer dispersions in the form of non-aqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081.

Among the film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may especially be vinyl polymers or copolymers, especially acrylic polymers.

The vinyl Film-forming polymers may result from the polymerization of ethylenically unsaturated monomers containing at least one acidic group and/or esters of these acidic monomers and/or amides of these acidic monomers.

Monomers bearing an acidic group that may be used are $\alpha,\beta$-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a C1-C30 and preferably C1-C20 alkyl, (meth)acrylates of an aryl, in particular of a C6-C10 aryl, and (meth)acrylates of a hydroxyalkyl, in particular of a C2-C6 hydroxyalkyl.

The film-forming polymer may be chosen from block or random polymers and/or copolymers especially comprising polyurethanes, polyacrylics, silicones, fluoro polymers, butyl rubbers, ethylene copolymers, natural gums and polyvinyl alcohols, and mixtures thereof.

The vinyl film-forming polymers may also result from the homopolymerization or copolymerization of monomers chosen from vinyl esters and styrene monomers.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and $\alpha$-methylstyrene.

Among the film-forming polycondensates that may be mentioned are polyurethanes, polyesteramides, polyamides, epoxyester resins, polyureas and polyesters.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an $\alpha$-olefin (containing from 8 to 28 carbon atoms), an alkyl vinyl ether (in winch the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an $\alpha$-olefin, an alkyl vinyl ether or an allylic or methallylic ester.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from copolymers of polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly (meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of C2-C20 alkenes, such as polybutene, alkylcelluloses with a linear or branched, saturated or unsaturated C1-C8 alkyl radical, for instance ethylcellulose and propylcellulose.

A preferred at least one film forming polymer for use in the compositions of the present invention is chosen from copolymers of vinyl acetate and copolymers of vinylpyrrolidone such as allyl stearate/vinyl acetate copolymer, commercially available from Chimex under the trade name Mexomere PQ®, VP/hexadecene copolymer, commercially available from international Specialty Products (ISP) under the trade names Antaron® V 216 or Ganex® V 216, and VP/eicosene copolymer, commercially available from ISP under the trade names Antaron® V 220 or Ganex® V 220.

The at least one film-forming polymer may be present in the composition of the present invention in an amount ranging from about 0.1% to about 30% by weight; such as from about 0.5% to about 20% by weight; such as from about 1% to about 10% by weight based on the total weight of the composition, including all ranges and subranges therebetween.

Styling Polymers

The styling polymers may be chosen from nonionic, anionic, cationic, and amphoteric polymers and mixtures thereof. The styling polymer may additionally be halogenated, in particular fluorinated.

The styling polymers can be used in solubilized form or else in the form of dispersions of solid polymer particles (latex or pseudo-latex).

The nonionic styling polymers useful according to the present invention are polyurethanes and N-vinylpyrrolidone polymers and copolymers. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Particularly preferred styling polymers are polyvinylpyrrolidone, vinylpyrrolidone/vinyl acetate copolymer, AMP-acrylates/allyl methacrylate copolymer (commercially available front Noveon under the tradename, Fixate G-100), sodium polystyrene sulfonate (commercially available from National Starch under the tradename, Flexan II), Vinylpyrrolidone/acrylates/lauryl methacrylate copolymer (commercially available from ISP under the tradename, Acrylidone LM), polyquaternium-6, and polyurethane-2 (commercially available from Noveon under the tradename, Avalure 405 or 410).

Preservatives

Suitable traditional preservatives for compositions of this invention are alkyl esters of para-hydroxybenzoic acid. Other preservatives which have more recently come into use include hydantoin derivatives such as 1,3-bis(hydroxymethyl)-5,5-dimethylhydantoin, propionate salts, and a variety of quaternary ammonium compounds such as benzalkonium chloride, quaternium 15 (Dowicil 200), benzethonium Chloride, and methylbenzethonium chloride. Cosmetic chemists are familiar with appropriate preservatives and routinely choose them to satisfy the preservative challenge test and to provide product stability. Suitable preservatives are benzyl alcohol, mixture of ethylhexylglycerin with benzyl alcohol, 2-bromo-2 nitropropane 1,3 diol, disodium EDTA, phenoxyethanol, mixture of phenoxyethanol and ethylhexylglycerin, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Actives

The additional active agents may be selected especially from among moisturizers, desquamating agents, agents for improving the skin barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-Seborrhoeic agents, astringents, cicatrizing agents, anti-inflammatory agents and anti-acne agents.

One skilled in this art will select the said active agent(s) as a function of the effect desired on the skin, the hair, the eyelashes, the eyebrows and the nails.

For caring for and/or making up aged skin, one will preferably select at least one active agent selected from among moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, and agents for promoting the cutaneous microcirculation for the area around the eyes.

The composition may also comprise at least one ingredient such as fillers with a soft-focus effect or agents for promoting the natural coloration of the skin, useful for complementing the biological effects of these active agents or for providing an immediate visual anti-aging effect.

For caring for and/or making up greasy skin, one skilled in tins art will preferably select at least one active agent selected from among desquamating agents, sebo-regulating agents or anti-seborrhoeic agents, and astringents.

The composition may also comprise at least one additional ingredient for complementing the biological effect of these active agents or for providing an immediate visual effect; especially exemplary are matting agents, fillers with a soft-focus effect, fluorescers, agents for promoting the naturally pinkish coloration of the skin, and abrasive fillers or exfoliants.

The composition of the present invention has low viscosity and can be used to formulate a wide variety of ingredients, such as fatty substances, humectants, solid particles, silicones, organic or inorganic sunscreens, without the need of dispersants or emulsifiers.

Anti-Perspirants:

In one useful embodiment, an antiperspirant composition comprises the silicone component of the present invention and one or more active antiperspirant agents. Suitable antiperspirant agents include, for example, the Category 1 active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

Fragrance Oils

In another useful embodiment, the compositions of the present invention are utilized in conjunction with fragrant materials. These fragrant materials may be fragrant compounds, encapsulated fragrant compounds or fragrance releasing compounds that, either the neat compounds or are encapsulated.

In Further Embodiment, the Personal Care Composition of the Present Invention Further Comprises Vitamins, Hormones, Enzymes, In one embodiment there is provided a personal care application comprising a silicone compound of the general formula (I) made by the process described herein. Some examples of such personal care applications comprising the silicone compound of the general formula (I) can be skin care products, sun care products, color cosmetic products, hair care products and luster enhancers.

In one non-limiting embodiment herein, the personal care application is a sun care product wherein the silicone compound of the general formula (I) is present, in en amount effective to increase the SPF of the sun care application. In one non-limiting embodiment, such SPF Increasing amounts of silicone containing compound of the general formula (I) comprises from about 0.1 to about 30 weight percent, more specifically from about 0.5 to about 20 weight percent and most specifically from about 1 to about 10 weight percent based on the weight of the sun care product formulation. The amount of increase in the SPF can be from 1 to about 50, more specifically from 1 to about 30 and most specifically from 1 to about 20 of SPF units.

As stated above, there is provided herein a process of preparing the silicone compound of the general, formula (I) for use in personal care applications. One embodiment of such a process is the process of making the silicone compound of the general formula (I), e.g., 1,1,1-triphenyl-3,3-dialkyl-3-alkenyldisiloxane, which comprises the reaction of triphenylsilanol with 1,1,3,3-tetraalkyl-1,3-dialkenyldisilazane and/or alkenyldialkylhalosilane to produce 1,1,1-triphenyl-3,3-dialkyl-3-alkenyldisiloxane, wherein each of the alkyl groups and ranges of carbon atoms in said alkyl group are such as those described herein, e.g., methyl, and wherein the alkenyl groups, and ranges of carbon atoms in said, alkenyl groups are such, as those described herein, e.g., vinyl.

In another embodiment, herein there is provided a process of making a silicone compound of the general formula (I) which comprises reacting 1,1,1-triphenyl-3,3-dialkyl-3-alkenyldisiloxane with a hydrogen siloxane to produce the silicone compound of the general formula (I), wherein the alkyl groups of the 1,1,1-triphenyl-3,3-dialkyl-3-alkenyldisiloxane are such as those alkyl groups defined elsewhere herein, such as the non-limiting example of methyl.

In one embodiment herein the hydrogen siloxane can be any siloxane compound that contains silyl-hydride moieties, and in one embodiment such hydrogen siloxane compound is selected from the group consisting of

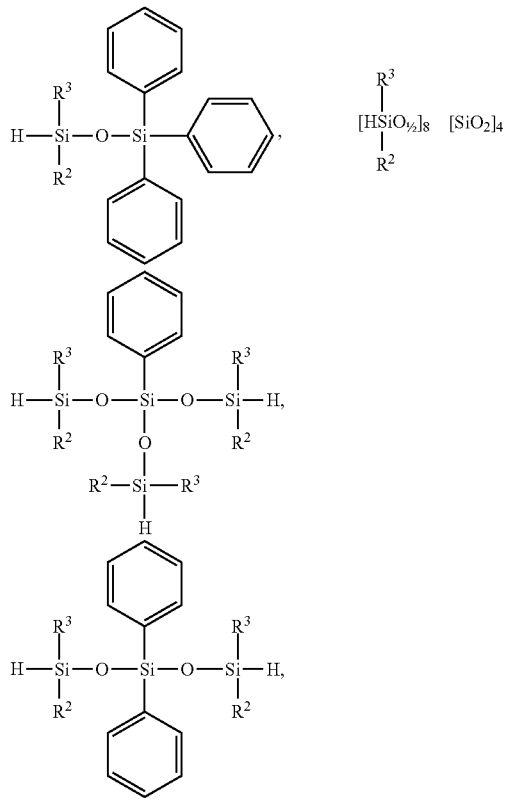

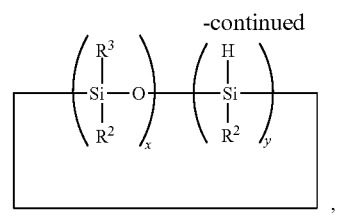

where x is 2 and y is 2,

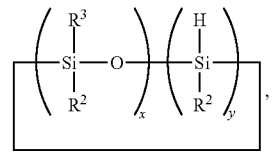

where x is 1 and y is 3, and

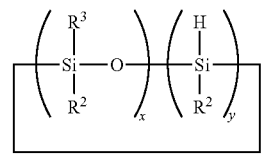

where x is 0 and y is 4,

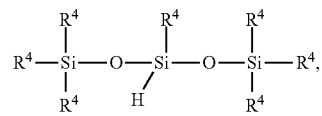

where each $R^4$ is independently a monovalent hydrocarbon group containing up to about 6 carbon atoms, and

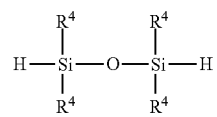

and wherein each $R^2$, $R^3$ and $R^4$ is independently a monovalent hydrocarbon group containing up to about 6 carbon atoms, more specifically up to about 4 carbon atoms, and most specifically methyl or ethyl.

In yet another embodiment there is provided a process of making the silicone compound of the general formula (I), wherein the process comprises reacting a 1,1,1-triphenyl-3,3-dialkyl-3-hydride disiloxane with an alkenyl compound containing from 2 to 10 carbon atoms, e.g., a linear alkenyl compound, more specifically wherein the alkenyl compound contains from 4 to 10 carbon atoms, even more specifically from 4 to 8 carbon atoms, or in another embodiment from 6 to 8 carbon atoms, and is terminally unsaturated, in one embodiment terminally unsaturated at one end, and in another embodiment terminally unsaturated at both ends. In one non-limiting embodiment the alkenyl compound is 1-octene and in another embodiment the alkenyl compound is 1,7-octadiene.

In one embodiment, the amounts of silicone compound of the general formula in the personal care composition described herein can comprise from about 0.1 weight percent to about 80 weight percent, more specifically from about 0.1 weight percent to about 40 weight percent and most specifically from about 0.1 weight percent to about 20 weight percent, based on the total weight of the personal care composition or the total weight of the personal care application.

In one embodiment herein, the amount of solvent that can be employed in the process(es) and compositions described herein comprise from about 10 weight percent to about 90 weight percent, more specifically from about 20 weight percent to about 70 weight percent and most specifically from about 30 weight percent to about 60 weight percent, said weight percents being based on the total weight of the silicone compound of the general formula (I) or the total weight of the personal care composition.

In one embodiment, the process of reacting triphenylsilanol with 1,1,3,3-tetraalkyl-1,3-dialkenyldisilazane and/or alkenyldialkylhalosilane to produce 1,1,1-triphenyl-3,3-dialkyl-3-alkenyldisiloxane, can comprise reacting triphenylsilanol with 1,1,3,3-tetraalkyl-1,3-dialkenyldisilazane and/or alkenyldialkylhalosilane in a molar ratio of 1:0.1 to 1:10, more specifically from about 1:0.5 to 1:5 and most specifically from about 1:0.5 to 1:2 of triphenylsilanol to combined molar amount of 1,1,3,3-tetraalkyl-1,3-dialkenyldisilazane and/or alkenyldialkylhalosilane. In one embodiment the amount of 1,1,3,3-tetraalkyl-1,3-dialkenyldisilazane in a combination of 1,1,3,3-tetraalkyl-1,3-dialkenyldisilazane and alkenyldialkylhalosilane can comprise from about 0 mole percent to about 100 mole percent, more-specifically from about 10 mole percent to about 90 mole percent and most specifically from about 20 mole percent to about 80 mole percent. In one embodiment the process can comprise reaction of triphenylsilanol with only 1,1,3,3-tetraalkyl-1,3-dialkenyldisilazane or with only alkenyldialkylhalosilane, and in such a process the molar ratio amounts of triphenyl silanol to dialkenyldisilazane or alkenyldialkylhalosilane can comprise those ratios described above for reaction of triphenylsilanol with 1,1,3,3-tetraalkyl-1,3-dialkenyldisilazane and/or alkenyldialkylhalosilane. In one embodiment herein the reaction of triphenylsilanol with 1,1,3,3-tetraalkyl-1,3-dialkenyldisilazane and/or alkenyldialkylhalosilane can be conducted in a solvent and/or in the presence of a catalyst as described herein, wherein the solvent and/or catalyst is present in an amount that provides for the weight percent of solvent and the amount of catalyst described herein as being present in the silicone composition.

In one other embodiment herein, the process of reacting 1,1,1-triphenyl-3,3-dialkyl-3-alkenyldisiloxane with hydrogen siloxane to produce silicone compound containing at least one silicone moiety can comprise employing 1,1,1-triphenyl-3,3-dialkyl-3-alkenyldisiloxane in a molar ratio to hydrogen atom of hydrogen siloxane of from about 100:1 to about 3:1, more specifically from about 50:1 to about 1:1 and most specifically from about 10:1 to about 1:1. Such a process can also be conducted in the presence of solvent and/or catalyst, in the amounts described herein.

In one specific embodiment herein the process(es) described herein can be conducted at a temperature of from about 0° C. to about 200° C., more specifically, from about 25° C. to about 150° C. and most specifically from about from about 50° C. to about 120° C., and at a pressure of from about 0.001 atm to about 5 atm, more specifically of from about 0.07 atm to about 3 atm and most specifically of from about 0.15 atm to about 2 atm.

In one specific embodiment herein the process(es) described herein can be conducted for a period of from about 1 minute to about 48 hours, more specifically from about 10 minutes to about 24 hours and most specifically from about 30 minutes to about 10 hours.

It will be understood herein that the respective R values, $R^1$ values, G definition, subscripts and other variables defined herein can have the same definitions in the process embodiments herein as these variables have in the composition embodiments described herein.

EXAMPLES

The following examples exemplify, but do not limit, the present invention.

Synthesis of organosiloxanes having high refractive index

Example 1

Preparation of S-1

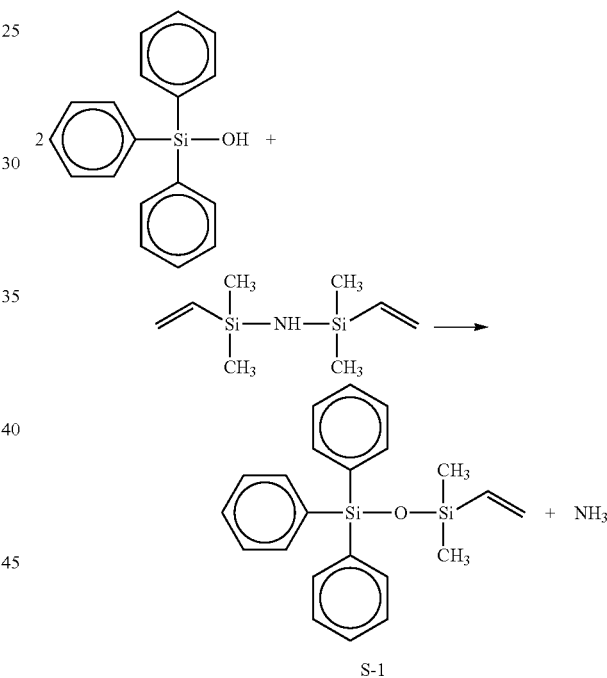

To a stirred, solution of 800 grams (2.89 mol) of triphenylsilanol in 1200 grams of toluene at 75° C. was added a mixture of 269 grams (1.45 mol) of 1,1,3,3-tetramethyl-1, 3-divinyldisilazane and 88 grams (0.73 mol) of vinyldimethylchlorosilane over a period of 30 minutes. After complete addition, the mixture was stirred for an additional a hours at 75° C. to complete a reaction, and then cooled to room temperature. The siloxane in toluene solution was washed 2 times with 1500 ml water. The final separation provided a water layer that was very near neutral in pH. The toluene solution was then heated to 130° C. and stripped at reduced pressure to remove the toluene, leaving 984 grams (94% of theory) of a clear, colorless product with n25/D=1.564 and a viscosity of 40 cSt. This product was identified as S-1 (1,1,1-triphenyl-3,3-dimethyl-3-vinyldisiloxane) by 1H-NMR and 29Si-NMR analysis.

Example 2

Preparation of H-1

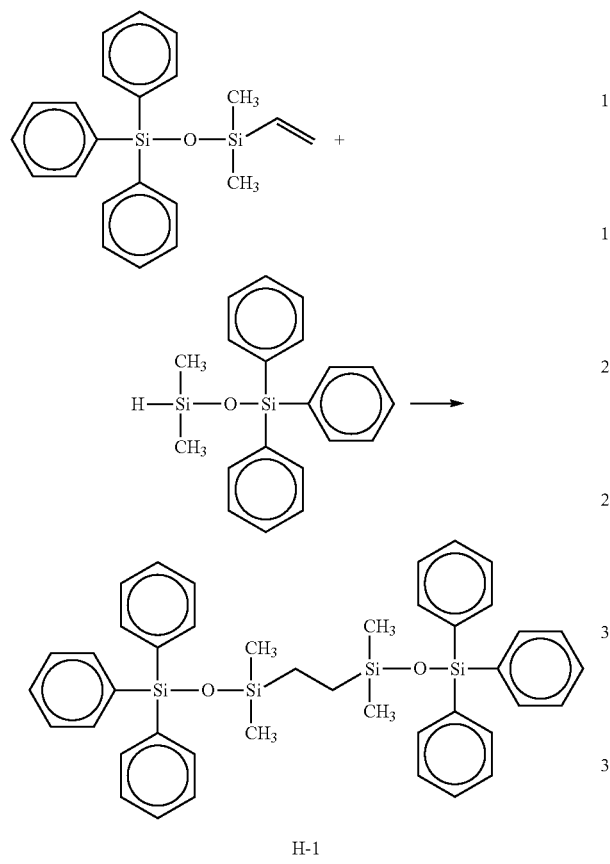

H-1

To a stirred mixture of 5 grams (0.014 mol) of S-1 prepared in example 1, 10 grams of toluene and platinum catalyst shown by Karstedt, U.S. Pat. No. 3,775,452 (i.e., Platinate(2-), hexachloro-, dihydrogen, (OC-6-11)-, reaction products with 2,4,6,8-tetraethenyl-2,4,6,8-tetramethylcyclotetrasiloxane was used), to provide 5 ppm of Pt catalyst based on a total amount of S-1 and hydrogen siloxane at 60° C. was added 4.6 grams (0.014 mol) of 1,1,1-triphenyl-3,3-dimethyldisiloxane over a period of 10 minutes. An exotherm was observed during the addition to about 80° C. After complete addition, the mixture was stirred for an additional 1 hour at 80° C. to complete a hydrosilylation reaction. The toluene solution was then heated to 120° C. and stripped at reduced pressure to remove the toluene, leaving 9 grams (94% of theory) of a white crystalline product with n25/D=1.536 in 50% toluene solution and a melting point of 95-99° C. This product was identified as H-1 by 1H-NMR analysis.

Example 3

Preparation of H-2

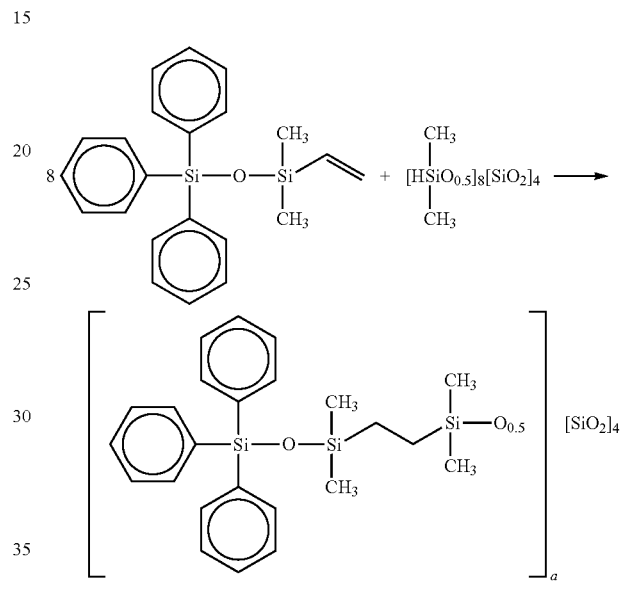

H-2

A procedure similar to Example 2 was performed, except that 2 grams (0.003 mol) of a hydrogen siloxane was used having a general formula of $[HSiMe_2O_{0.5}]_8[SiO_2]$, 7.8 grams (0.022 mol) of S-1. There was obtained 9.0 grams (92% of theory) of a slightly hazy product, with n25/D=1.556 and a viscosity of 17,000 cP. This product was identified as H-2 by 1H-NMR analysis.

Example 4

Preparation of H-3

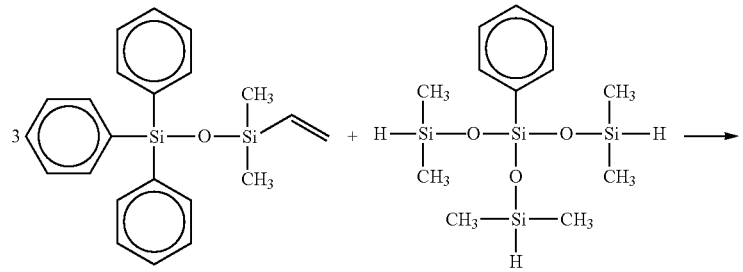

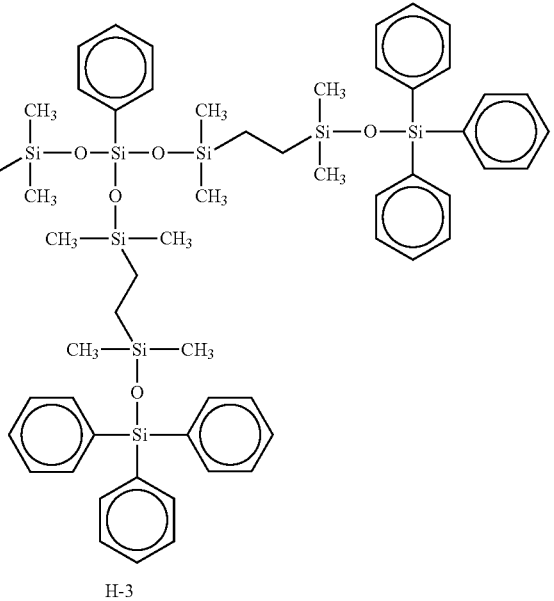

H-3

A procedure similar to Example 2 was performed, except that 4.4 grams (0.013 mol) of a hydrogen siloxane was used having a formula of PhSi—[OSiMe$_2$H]$_3$ (wherein Ph is phenyl and Me is methyl), 133 grams (0.37 mol) of S-1, 150 grams of toluene. There was obtained 160 grams (92% of theory) of a slightly hazy product with n25/D=1.558 and a viscosity of 4,400 cP. This product was identified as H-3 by 1H-NMR analysis.

Example 5

Preparation of H-4

A procedure similar to Example 2 was performed, except that 4.4 grams (0.013 mol) of a hydrogen siloxane was used having a formula of Ph$_2$Si[OSiMe$_2$H]$_2$ (wherein Ph is phenyl and Me is methyl), 10 grams (0.028 mol) of S-1. There was obtained 13.5 grams (94% of theory) of a white crystalline product with n25/D=1.528 in 50% toluene solution and a melting point of 60-65° C. This product was identified as H-4 by 1H-NMR analysis.

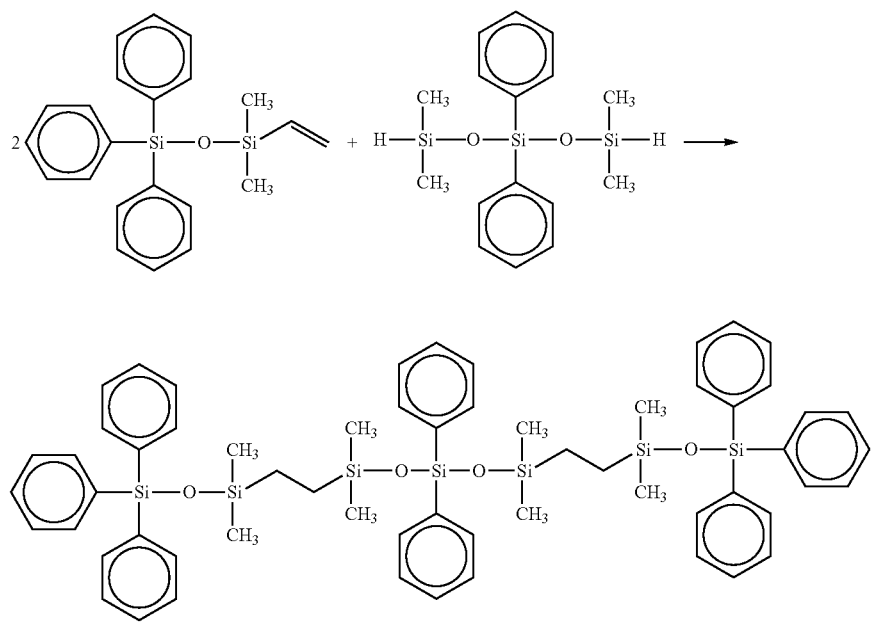

H-4

Example 6

Preparation of H-5

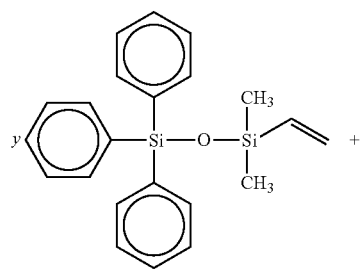

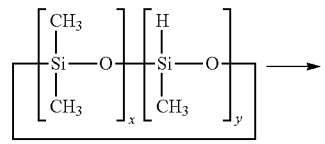

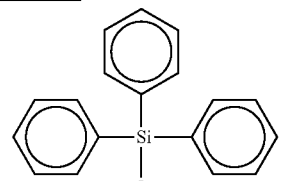

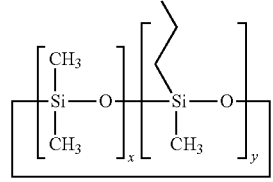

H-5: x = 2, y = 2
H-6: x = 1, y = 3
H-7: x = 0, y = 4

A procedure similar to Example 2 was performed, except that 43 grams (0.16 mol) of a 2,2,4,4,6,6,8,8-hexamethylcyclotetrasiloxane was used as a hydrogen siloxane, 121.5 grams (0.34 mol) of S-1, 150 grams of toluene. There was obtained 160 grams (97% of theory) of a clear, colorless product with n25/D=1.539 and a viscosity of 1,900 cP. This product was identified as H-5 by 1H-NMR analysis.

Example 7

Preparation of H-6

A procedure similar to Example 2 was performed, except that 30 grams (0.12 mol) of a 2,2,4,4,6,6,8-pentamethylcyclotetrasiloxane was used as a hydrogen siloxane, 133.9 grams (0.37 mol) of S-1, 150 grams of toluene. There was obtained 156 grams (95% of theory) of a clear, colorless product with n25/D=1.555 and a viscosity of 12,900 cP. This product was identified as H-6 by 1H-NMR analysis.

Example 8

Preparation of H-7

A procedure similar to Example 2 was performed, except that 23 grams (0.10 mol) of a 2,4,6,8-tetramethylcyclotetrasiloxane was used as a hydrogen siloxane, 144.8 grams (0.40 mol) of S-1, 150 grams of toluene. There was obtained 160 grams (95% of theory) of a clear, colorless product with n25/D=1.565 and a viscosity of 56,900 cP. This product was identified as H-7 by 1H-NMR analysis.

Example 9

Preparation of H-8

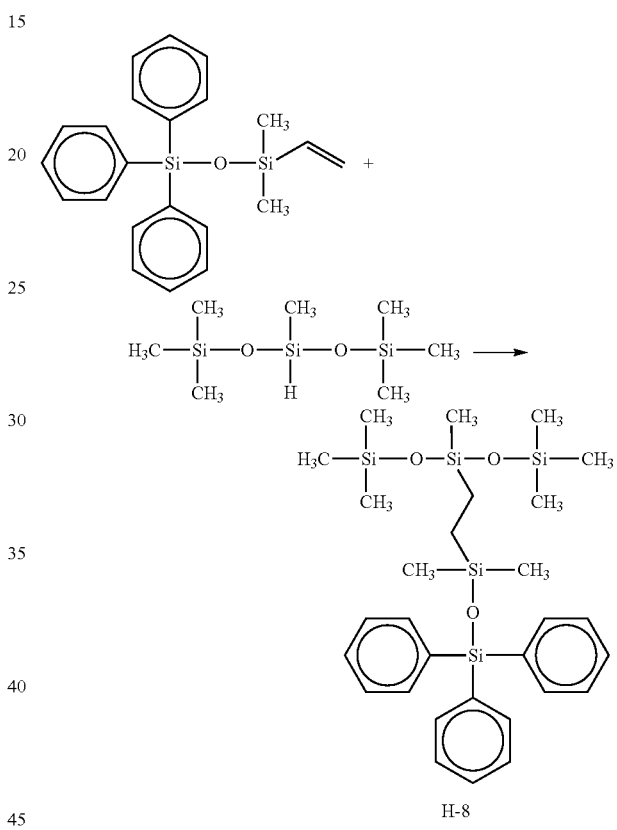

H-8

A procedure similar to Example 2 was performed, except that 50 grams (0.23 mol) of a 1,1,1,3,5,5,5-heptamethytrisiloxane was used as a hydrogen siloxane, 85 grams (0.24 mol) of S-1, 130 grams of toluene. There was obtained 128 grams (95% of theory) of a clear, colorless product, with n25/D=1.507 and a viscosity of 47 cSt. This product was identified as H-8 by 1H-NMR analysis.

Example 10

Preparation of H-9

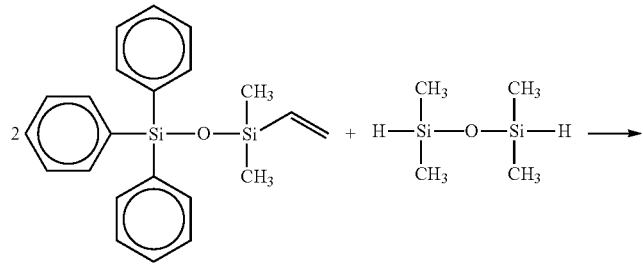

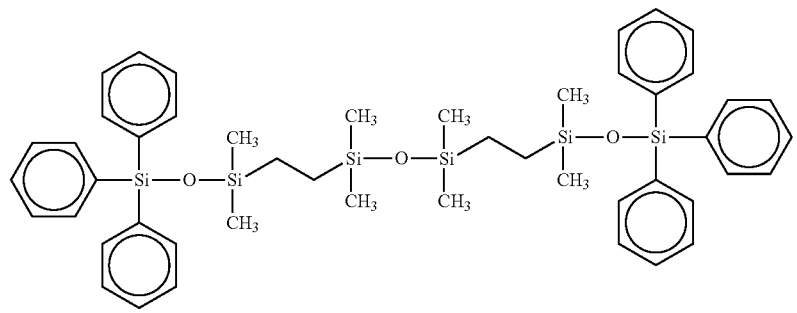

H-9

A procedure similar to Example 2 was performed, except that 20 grams (0.15 mol) of a 1,1,3,3-tetramethydisiloxane was used as a hydrogen siloxane, 113 grams (0.31 mol) of S-1, 130 grams of toluene. There was obtained 126 grams (95% of theory) of a clear, colorless product with n25/D=1.554 and a viscosity of 350 cP. This product, was identified as H-9 by 1H-NMR analysis.

Example 11

Preparation of H-10

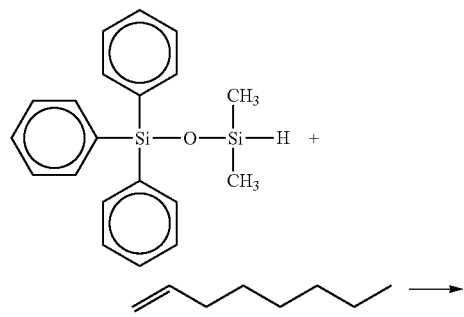

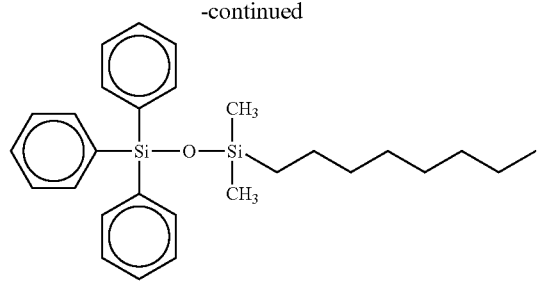

H-10

To a stirred mixture of 1 grams (0.009 mol) of 1-octene, 5 grams of toluene and platinum catalyst shown by Karstedt, U.S. Pat. No. 3,775,452 (Platinate(2-), hexachloro-, dihydrogen, (OC-6-11)-, reaction products with 2,4,6,8-tetraethenyl-2,4,6,8-tetramethylcyclotetrasiloxane), to provide 5 ppm of Pt catalyst based on a total amount of 1-octane and 1,1,1-triphenyl-3,3-dimethyldisiloxane at 70° C. was added 2 grams (0.006 mol) of 1,1,1-triphenyl-3,3-dimethyldisiloxane in 2 grams toluene solution over a period of 5 minutes. An exotherm was observed during the addition to about 75° C. After complete addition, the mixture was stirred for an additional 6 hours at 75° C. to complete a hydrosilylation reaction. The toluene solution was then heated to 120° C. and stripped at reduced pressure to remove the toluene and the excess of 1-octene, leaving 2.4 grams (90% of theory) of a clear, pale yellow product with n25/D=1.536 and a viscosity of 40 cP. This product was identified as H-10 by 1H-NMR analysis.

Example 12

Preparation of H-11

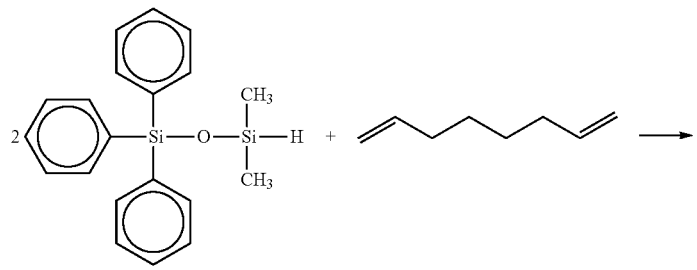

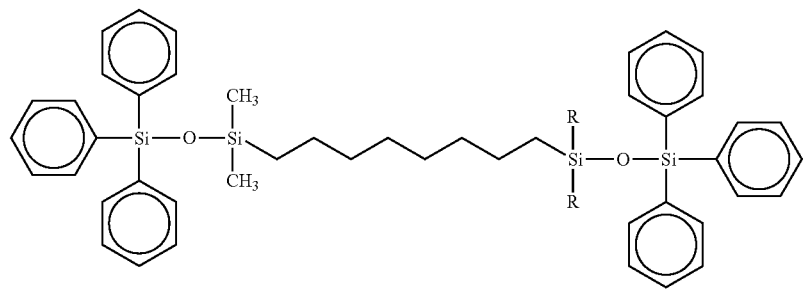

H-11

To a stirred mixture of 0.82 grams (0.007 mol) of 1,7-octadiene, 5 grams of toluene and platinum catalyst shown by Karstedt, U.S. Pat. No. 3,775,452 (Platinate(2-), hexachloro-, dihydrogen, (OC-6-11)-, reaction products with 2,4,6,8-tetraethenyl-2,4,6,8-tetramethylcyclotetrasiloxane), to provide 10 ppm of Pt catalyst based on a total amount of 1,7-octadiene and 1,1,1-triphenyl-3,3-dimethyldisiloxane at 70° C. was added 5 grams (0.015 mol) of 1,1,1-triphenyl-3,3-dimethyldisiloxane in 5 grams toluene solution over a period of 10 minutes. An exotherm was observed during the addition to about 73° C. After complete addition, the mixture was stirred for an additional 24 hours at 90° C. to complete a hydrosilylation reaction. The toluene solution was then heated to 120° C. and stripped at reduced pressure to remove the toluene, leaving 5.4 grams (93% of theory) of a clear, pale yellow product with n25/D=1.565 and a viscosity of 1100 cP. This product was identified as H-11 by 1H-NMR analysis.

Results

TABLE 1

Synthesis result

| Product | Appearance | Viscosity [Centipoise, 25° C.] | Melting Point [° C.] | Refractive Index [25° C.] |
|---|---|---|---|---|
| S-1 | Clear, colorless | 40* | — | 1.564 |
| H-1 | White crystalline | — | 95-99 | 1.536** |
| H-2 | Slightly hazy | 17,000 | — | 1.556 |
| H-3 | Slightly hazy | 4,400 | — | 1.558 |
| H-4 | White crystalline | — | 60-65 | 1.528** |
| H-5 | Clear, colorless | 1,900 | — | 1.539 |
| H-6 | Clear, colorless | 12,900 | — | 1.555 |
| H-7 | Clear, colorless | 56,900 | — | 1.565 |
| H-8 | Clear, colorless | 47 | — | 1.507 |
| H-9 | Clear, colorless | 350 | — | 1.554 |

*viscosity is in cSt - Viscosity was measured using Cannon-Fenske viscometer.
cP(Centipoise) - viscosity was measured using Vismetron viscometer, VSA-L model (similar to Blookfield viscometer, LVT model)
**refractive index is measured with 50% toluene solution Migration Property
Procedure;
(1) 0.3 g of the sample was put on the synthetic skin (supplier; IDEMITSU TECHNOFINE Co., Ltd.). SF1550 (phenyltrimethicone) and Dimethicone (10,000 cSt) were compared.

(2) The state of oil droplet was determined immediately.
(3) The synthetic skin was left out at ambient temperature.
(4) The state of oil droplet was observed after 24 hours.

Test results showed as demonstrated in FIG. 1 that organosiloxanes (S-1 and H-5-7) having non-migration properties. Without bound to any theory, it is believed that the migration or spreading of liquid on skin surface or through skin textures such as wrinkles is governed by surface tension of liquid. Previously reported critical surface tension ($g_c$) is between 24-27 dynes/cm for human skirt and is 26 dynes/em for human hair (50-100% relative humidity). Liquids higher surface tension than $g_c$ will exhibit non-migrating and non-feathering properties. It is discovered that these phenyl fluids have higher surface tension than $g_c$ and thus show non-migrating and non-feathering properties.

| | Fluid | | | | |
|---|---|---|---|---|---|
| | S-1 | H-5 | H-6 | SF1550 | PDMS 50 |
| Surface tension (dynes/cm) | 30.14 | 27.9 | 29.6 | 22.2 | 20.8 |

Lip Gloss: Examples 11 to 17, Comparative Examples 1 to 2

Procedure:

1. The ingredients were added in the order listed and heated to 80° C.

2. The mixture was mixed until uniform and cooled to room temperature.

Evaluation 10 of the panelists evaluated the lip gloss and then rated the performance on a scale of 1-5 (1: not good, 3: good, 5; excellent)

The score given was an average of the scores of the 10 panelists.

TABLE 2

Lip Gloss composition (wt %)

| Lip Gloss | Example 11 | 12 | 13 | 14 | 15 | 16 | 17 | Comparative Example 1 | 2 |
|---|---|---|---|---|---|---|---|---|---|
| Ingredient | | | | | | | | | |
| S-1 | 40 | 20 | | | | | | | |
| H-4 | | 20 | | | | | | | |
| H-5 | | | 40 | | | | | | |
| H-7 | | | | 40 | 30 | 5 | 20 | | |
| Phenyltrimethicone, SF1550 (1) | | | | | 10 | | | 40 | |
| Diphenyldimethicone, TSF433 (1) | | | | | | | | | 40 |
| Hydrogenated Polyisobutene, Parleam 18 (2) | 50 | 50 | 50 | 50 | 50 | 85 | 70 | 50 | 50 |
| Glyceryl Isostearate | 4 | 4 | 4 | 4 | 4 | 4 | 4 | 4 | 4 |
| Triisostearin | 4 | 4 | 4 | 4 | 4 | 4 | 4 | 4 | 4 |
| Diisostearyl Malate | 2 | 2 | 2 | 2 | 2 | 2 | 2 | 2 | 2 |
| Score | | | | | | | | | |
| Shine after application | 4.5 | 4.3 | 4.5 | 4.6 | 4.4 | 4.1 | 4.3 | 2.7 | 3.4 |
| Durability of shine | 4.4 | 4.2 | 4.4 | 4.6 | 4.3 | 4.0 | 4.3 | 2.1 | 2.9 |

(1) Momentive
(2) NOF Corporation

Leave on Conditioner: Examples 18 to 24, Comparative Examples 3 to 4

Procedure:
1. The ingredients were added in the order listed and heated to 60° C.
2. The mixture was mixed until uniform and cooled to room temperature.
3. 0.5 g of the leave on conditioner was uniformly applied to 10 g of Asian hair tress.
4. The 10 panelists evaluated the hair shine.

Evaluation:

10 of the panelists evaluated the leave on conditioner and then rated the performance on a scale of 1-5 (1: not good, 3: good, 5: excellent).

The score given was an average of the scores of the 10 panelists.

TABLE 3

Leave on conditioner composition (wt %)

| Leave on conditioner | Example 18 | 19 | 20 | 21 | 22 | 23 | 24 | Comparative Example 3 | 4 |
|---|---|---|---|---|---|---|---|---|---|
| Ingredient | | | | | | | | | |
| S-1 | 30 | 15 | | | | | | | |
| H-4 | | 15 | | | | | | | |
| H-5 | | | 30 | | | | | | |
| H-7 | | | | 30 | 20 | 5 | 10 | | |
| Phenyltrimethicone, SF1550 (1) | | | | | 10 | | | 30 | |
| Diphenyldimethicone, TSF433 (1) | | | | | | | | | 30 |
| Dimethicone, TSE200A (1) | 9 | 9 | 9 | 9 | 9 | 9 | 9 | 9 | 9 |
| Hydrogenated Polyisobutene, IP solvent 2028MU (2) | 61 | 61 | 61 | 61 | 61 | 86 | 81 | 61 | 61 |
| Score | | | | | | | | | |
| Shine after application | 4.3 | 4.2 | 4.4 | 4.7 | 4.4 | 4.2 | 4.3 | 2.3 | 3.0 |
| Durability of shine | 4.1 | 4.2 | 4.2 | 4.6 | 4.3 | 4.1 | 4.2 | 1.9 | 2.7 |

(1) Momentive
(2) Idemitsu Kosan Co., Ltd

Make-Up Foundation: Example 25
Procedure:
1. The ingredients of Part A were combined in the order shown, and after each component was added the mixture was thoroughly mixed until homogenous before adding the next ingredient. The mixture was then heated to 60° C. and mixed.
2. In a separate vessel, the ingredients of Part B were combined in the order shown.
3. Part B was the slowly added to Part A with good mixing.
4. The resultant mixture was poured into suitable containers.
Evaluation:
10 of the panelists evaluated make-up foundation and then rated the performance on a scale of 1-5 (1: not good, 3: good, 5: excellent)
The score given was an average of the scores of the 10 panelists.

TABLE 4

| Make-up Foundation composition | | |
|---|---|---|
| Part | Ingredient | Wt % |
| | Make-up Foundation | |
| A | S-1 | 20 |
| | Cyolopentasiloxane (and) PEG/PPG-20-15 Dimethicone, SF1540 (1) | 5 |
| | Cyclopentasiloxane (and) Dimethicone/Vinyl Dimethicone Crosspolymer, SFE839 (1) | 3 |
| | C30-45 Alkyl Dimethicone, SF1642 (1) | 2 |
| | Cyclopentasiloxane | 12 |
| | Titanium Dioxides | 5 |
| | Yellow Iron Oxides | 1.3 |
| | Red Iron Oxides | 0.6 |
| | Black Iron Oxides | 0.1 |
| | Sorbitan Oleate | 0.5 |
| B | Deionized Water | 49.3 |
| | Polysorbate-20 | 0.2 |
| | Sodium Chloride | 1 |
| | Score | |
| Natural gloss after application | | 4.4 |
| Durability of natural gloss | | 4.3 |

Sunscreen: Example 26
Procedure:
1. The ingredients of Part A were combined in the order shown and heated to 70° C.
2. Part B was mixed into Part A and mixed until uniform.
3. In a separate vessel, the ingredients of Part C were combined in the order shown and mixed until uniform and then Part C was added into Part A.
4. The resultant mixture was emulsified by a high shear mixer and cooled to room temperature.
Evaluation:
10 of the panelists evaluated sunscreen and then rated the performance on a scale of 1-5 (1: not good, 3: good, 5: excellent)
The score given was an average of the scores of the 10 panelists.

TABLE 5

| Sunscreen composition | | |
|---|---|---|
| Part | Ingredient | Wt % |
| | Sunscreen | |
| A | S-1 | 10 |
| | Polymethylsilsesquioxane, SilForm Flexible resin (1) | 2 |
| | Cyclopentasiloxane (and) PEG/PPG-20-15 Dimethicone, SF1540 (1) | 1.2 |
| | Cyclopentasiloxane (and) C30-45 Alkyl Cetearyl Dimethicone Crosspolymer, Velvesil 125 (1) | 4 |
| | Cyclopentasiloxane | 20 |
| | Caprylyl methicone, Silsoft 034 (1) | 0.7 |
| | Sorbitan sesquioleate | 1 |
| | Ethylhexyl methoxycinnamate | 7 |
| | Tocopherol | 0.1 |
| B | Polymethylsilsesquioxane, Tospearl 145A (1) | 4 |
| | Zinc oxide | 9 |
| C | EDTA disodium | 0.1 |
| | Sodium Chloride | 0.4 |
| | Glycerin | 2 |
| | Water | 33.4 |
| | Ethanol | 5 |
| | Phenoxyethanol | 0.1 |
| | Score | |
| Natural gloss after application | | 4.1 |
| Durability of natural gloss | | 4.1 |

(1) Momentive

Eye Shadow: Example 27
Procedure:
1. The ingredients of Part A were combined in the order shown and heated to 70° C. (Oil phase) and then mixed until uniform.
2. In a separate vessel, the ingredients of Part B were combined in the order shown, and heated to 70° C. and then mixed until uniform.
3. The ingredients of Part C were added into part B and mixed until uniform. (Water phase)
4. The water phase was added into the oil phase and emulsified by a high shear mixer.
5. The resultant mixture was cooled to room temperature.
Evaluation:
10 of the panelists evaluated eye shadow and then rated the performance on a scale of 1-5 (1: not good, 3: good, 5: excellent)
The score given was an average of the scores of the 10 panelists.

TABLE 6

| Eye Shadow composition | | |
|---|---|---|
| Part | Ingredient | Wt % |
| | Eye Shadow | |
| A | S-1 | 20 |
| | Stearic acid | 7 |
| | Isopropyl myristate | 1 |
| | Mineral oil | 4 |
| | Propylene glycol monolaurate | 1.5 |
| | Hydrogenated polyisobutene | 1 |
| | Phenoxyethanol | 0.1 |
| B | Water | 40.4 |
| | 1,3-butyleneglycol | 5 |
| | Triethanolamine | 1 |
| C | Talc | 10 |
| | Kaolin | 4 |
| | Pigment | 5 |
| | Score | |
| Natural gloss after application | | 4.6 |
| Durability of natural gloss | | 4.5 |

Hair Conditioner: Example 28
Procedure:
1. The ingredients of Part A were combined in the order shown and heated to 70° C. (Water phase)

2. In a separate vessel the ingredients of Part B were combined in the order shown, and heated to 70° C. and mixed until uniform. (Oil phase)
3. The oil phase was then added into the water phase.
4. The mixture was emulsified by a high shear mixer and cooled to room temperature.
5. 2 g of the conditioner was uniformly applied to 10 g of Asian hair tress.
6. The hair tress was rinsed 2 times by 40° C. water and dried.
7. The panelists then evaluated the hair conditioner.

Evaluation:
10 of the panelists evaluated hair conditioner and then rated the performance on a scale of 1-5 (1: not good, 3: good, 5: excellent)
The score given was an average of the scores of the 10 panelists.

TABLE 7

Hair Conditioner composition

| Part | Ingredient | Wt % |
|---|---|---|
| | Hair Conditioner | |
| A | Steartrimonium Chloride, 28% | 2.5 |
| | Glycerin | 3 |
| | Water | 87.9 |
| B | H-6 | 3 |
| | Mineral oil | 1 |
| | Cetyl alcohol | 1.5 |
| | Stearyl alcohol | 1 |
| | Phenoxyethanol | 0.1 |
| | Score | |
| Shine after application | | 4.4 |
| Durability of shine | | 4.2 |

Hair Shampoo: Example 29
Procedure:
1. The ingredients of part A were combined in the order shown and heated to 70° C. Mix until uniform.
2. The ingredients of Part B were added into part A and mixed until uniform.
3. The ingredients of part C were then added.
4. The mixture was then emulsified by a high shear mixer and cooled to room temperature.
5. 2 g of the hair shampoo was uniformly applied to 10 g of an Asian hair tress.
6. The hair tress was rinsed 2 times by 40° C. water and dried.
7. Panelists evaluated the hair shampoo.

Evaluation:
10 of the panelists evaluated hair shampoo and then rated the performance on a scale of 1-5 (1: not good, 3: good, 5: excellent)
The score given was an average of the scores of the 10 panelists.

TABLE 8

Hair Shampoo formulation

| Part | Ingredient | Wt % |
|---|---|---|
| | Hair shampoo | |
| A | Polyquaternium-10 | 0.5 |
| | Water | 41.9 |

TABLE 8-continued

Hair Shampoo formulation

| Part | Ingredient | Wt % |
|---|---|---|
| B | Sodium laureth sulfate, 27% | 33.0 |
| | Cocamidopropyl betaine, 30% | 15.0 |
| | Cocamide MEA | 1.5 |
| | Glycol distearate | 2.0 |
| | Glycerin | 3.0 |
| | Sodium Chloride | 0.5 |
| | Phenoxyethanol | 0.1 |
| C | S-1 | 2.5 |
| | H-7 | 0.5 |
| | Score | |
| Shine after application | | 4.1 |
| Durability of shine | | 4.1 |

Sunscreen: Example 30-32, Comparative example 5.
Procedure:
1. Mix all the ingredients except $TiO_2$ using a Speedmixer (Flaktek Inc.).
2. Mix at 300 rpm for 1 minute.
3. Add $TiO_2$ powder and mix in Flaktek at 300 rpm for another 2 minutes.
4. The comparative example contained dimethicone oil (5 cst) instead of the invented silicones.

Evaluation:
1. The spf of the sunscreen is in-vitro using artificial skin.
2. The skin is hydrated for 24 hrs. in water and glycerin mixture (70:30).
3. The formulation was applied 2 mg/cm$^2$.
4. The samples were allowed to dry for 2 hrs.
5. The spf was measured using Labsphere UV-
6. 1000S spectrophotometer.

TABLE 9

Sunscreen formulation with $TiO_2$

| Ingredients (wt. %) | Example | | | Comparative example |
|---|---|---|---|---|
| | Example 30 | Example 31 | Example 32 | Example 5 |
| Physical Sunscreen | | | | |
| S-1 | 7 | | | |
| H-5 | | 7 | | |
| H-6 | | | 7 | |
| Dimethicone (5 cst)[1] | | | | 7 |
| Velvesil* DM[1] | 51 | 51 | 51 | 51 |
| SilSoft* 034[1] | 25 | 25 | 25 | 25 |
| SR1000[1] | 2 | 2 | 2 | 2 |
| $TiO_2$ (MT 100-TV)[2] | 15 | 15 | 15 | 15 |
| Score | | | | |
| SPF | 48 | 49.7 | 46 | 38.5 |

[1]Momentive Performance Materials
[2]TRI-K Industries

Lip Stick: Example 33
Procedure:
1. Make a Pre-Mix of the Part A.
2. Mix Part A and Part B until a homogeneous mixture at 85° C.
3. Add Part C and continue mixing 85° C.
4. Add Part D and continue mixing at 85° C.
5. Add Part E and mix for a minute till homogeneous mixture is formed.

6. Pour into molds.
7. Wait 30 minutes (until thoroughly cooled and hardened) and unmold the lipsticks.

TABLE 10

Lip Stick Formulation.
Lip Stick

| Part | Ingredient | Wt. % |
|---|---|---|
| A | SilForm Flexible Resin (1) | 6 |
|   | Velvesil 034 (1) | 6 |
| B | Ozokerite Wax 77W | 1 |
|   | Shea Butter | 17.5 |
|   | Olive Oil | 5 |
|   | S-1 | 2.5 |
|   | White Beeswax | 3 |
|   | Softisan 649 (2) | 15.1 |
|   | Candelila Wax | 17.55 |
|   | Red Shade Dispersion | 4.7 |
| C | Softouch boron nitride CC6097 (1) | 5.8 |
| D | Sensiva SC10 (3) | 0.5 |
|   | Vitamin E Acetate | 0.85 |
| E | Silsoft ETS (1) | 14.5 |

(1) Momentive Performance Materials
(2) Peter Cremer USA
(3) Schülke

The above noted examples clearly demonstrate that the silicone composition described herein can be used in personal care applications with minimal migration and good shine and/or gloss.

While the invention has been described with reference to certain embodiments, it will be understood by those skilled in the art that various changes may be made and equivalents may be substituted for elements thereof without departing from the scope of the invention, in addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A silicone compound having a structure of general formula (I):

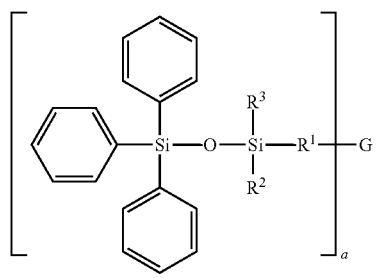
(I)

where each $R^2$ and each $R^3$ are independently selected from a monovalent hydrocarbon radical containing from 1 to about 8 carbon atoms, each $R^1$ is a divalent alkyl, alkene, arylene or alkyne group, each containing up to about 45 carbon atoms and G is hydrogen, an organic group or a silicon-containing group, and where subscript a is an integer of from 1 to 100, and wherein the silicone compound has a refractive index of greater than 1.50.

2. The silicone compound of claim 1 having the structure of general formula (I) where G is selected from the group consisting of:

(a) an organic group that is a linear or branched, unsaturated or saturated hydrocarbon radical containing up to about 1,000 carbon atoms, and optionally containing at least one of a heteroatom, a carbonyl group, an ester group, an amide group and a hydroxyl group with the valency of 1-25 subject to the limitation that the valance of the organic group is equal to the value of the subscript a;

(b) a cyclic siloxane with the general formula (II):

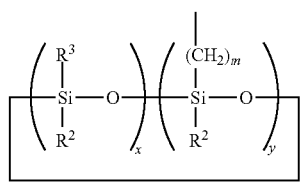
(II)

each $R^2$ and each $R^3$ are independently a monovalent hydrocarbon radical containing from 1 to about 8 carbon atoms, the subscript m is 2 to 6, the subscript x is 0-8 and the subscript y is 1-8, subject to the limitation that the value of subscript a=y; and, (c) a siloxane with the general formula (III):

$$M_b M^*_c D_d D^*_e T_f T^*_g Q_h A_i B_j C_k \quad (III)$$

where $M = R^4 R^5 R^6 SiO_{1/2}$, $M^* = R^4 R^* R^6 SiO_{1/2}$ $D = R^7 R^8 SiO_{2/2}$, $D^* = R^7 R^* SiO_{2/2}$ $T = R^9 SiO_{3/2}$, $T^* = R^* SiO_{3/2}$, $Q = SiO_{4/2}$, $A = O_{1/2} Si(R^{10})(R^{11}) R^{12} Si(R^{13})(R^{14}) O_{1/2}$ $B = O_{1/2} Si(R^{15})(R^{16}) R^{17} Si(R^{18}) O_{2/2}$ $C = O_{1/2} Si(R^{19})(R^{20}) R^{21} SiO_{3/2}$ where $R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$, and $R^{20}$ are each independently selected from the group consisting of $OR^{22}$ and a monovalent hydrocarbon radical containing from 1 to about 20 carbon atoms, optionally containing at least one of a heteroatom, an aromatic group, and a hydroxyl group, $R^{12}$, $R^{17}$, and $R^{21}$ are independently a divalent hydrocarbon group of from 1 to about 8 carbon atoms, $R^{22}$ is a monovalent hydrocarbon radical containing from 1 to about 20 carbon atoms, $R^*$ is a divalent hydrocarbon where one of the valences is bound to $R^1$, and subscripts b, c, d, e, f, g, h, i, j and k are zero or positive subject to the limitation b+c+d+e+f+g+h+i+j<1000 and c+e+g≥1 and c+e+g=a.

3. The silicon compound of claim 1 wherein the silicon-containing group is a silicone-containing group.

4. The silicone compound of claim 1 wherein the general formula (I) is such that a=1 and G is a linear or branched unsaturated hydrocarbon radical of up to 8 carbon atoms.

5. The silicone compound of claim 1 which is of the formula (IV):

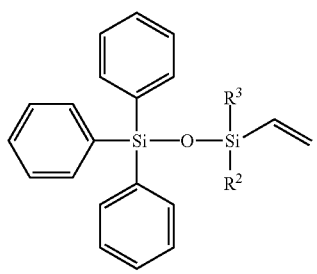
(IV)
wherein $R^2$ and $R^3$ are each independently an alkyl group of from 1 to 3 carbon atoms.
6. The silicone compound of claim 2 wherein the compound is of the general formula (III) and where the subscripts i+j+k≥1.
7. The silicone compound of claim 2 which is selected from the group consisting of:
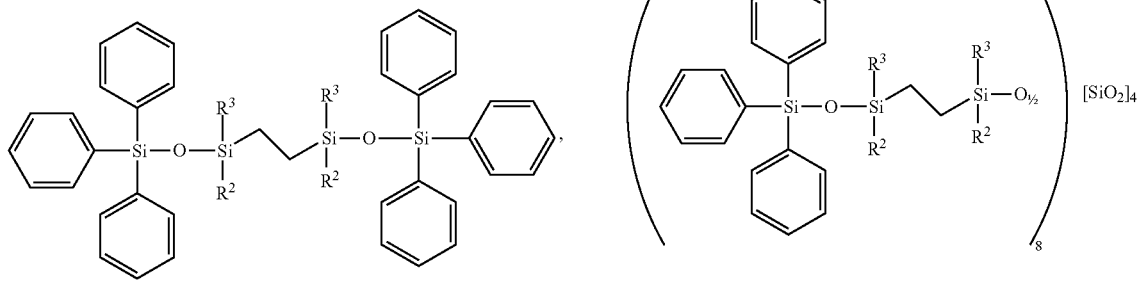
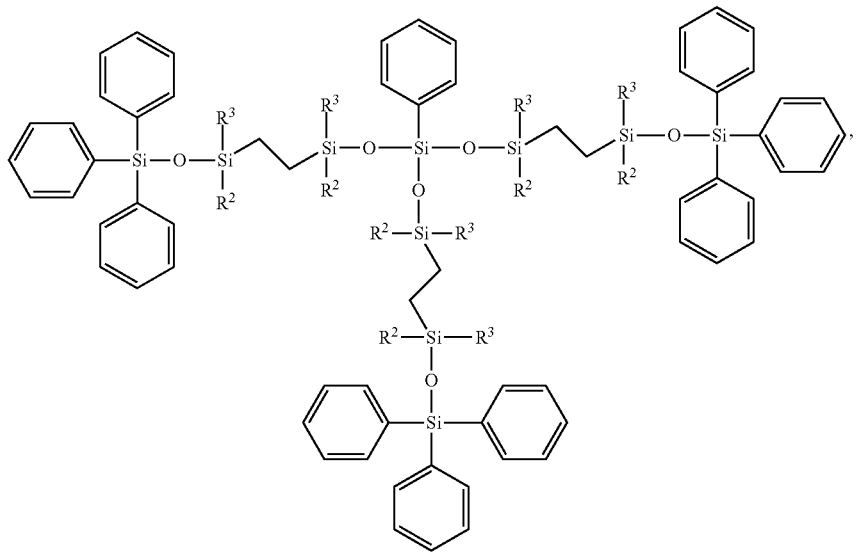
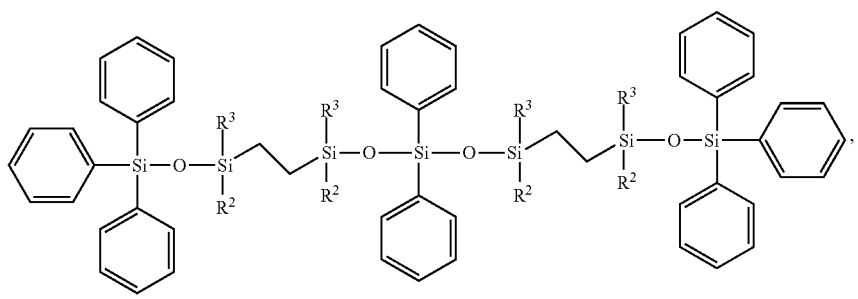

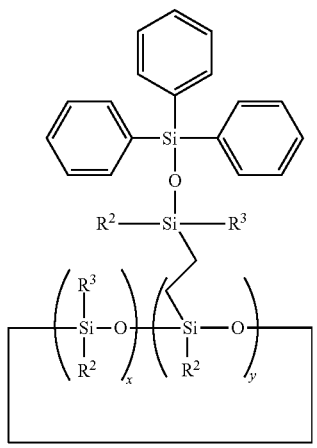
where x is 2 and y is 2,
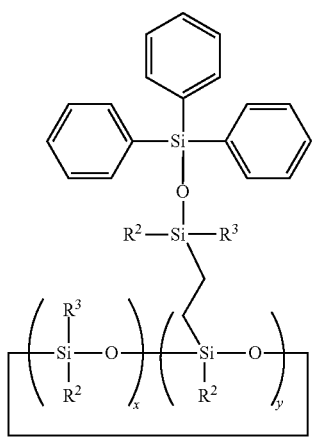
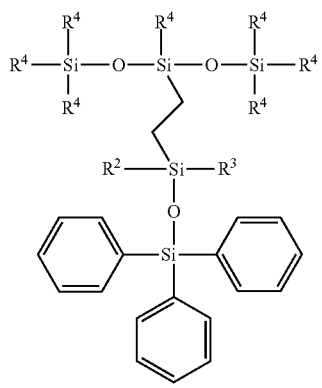
where x is 1 and y is 3, and
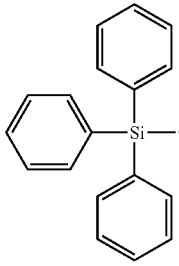
where y is 4,
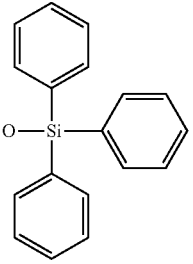
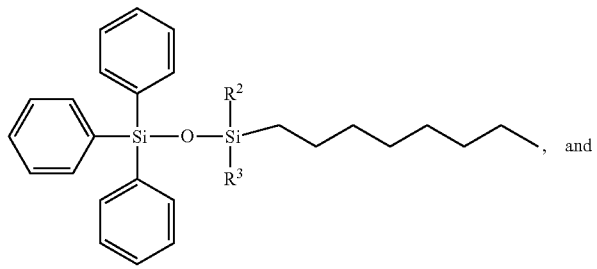
, and -continued

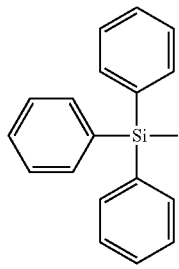 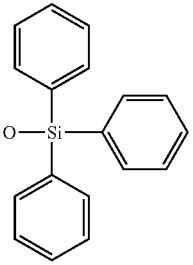

wherein in the foregoing formulae, each $R^2$, $R^3$ and $R^4$ are each independently a monovalent hydrocarbon radical containing up to about 6 carbon atoms.

8. The silicone compound of claim 7 wherein each $R^2$, $R^3$ and $R^4$ is methyl.

9. The silicone compound of claim 1 which has surface tension higher than 27 dynes/cm.

10. A personal care composition comprising a silicone compound having a structure of general formula (I):

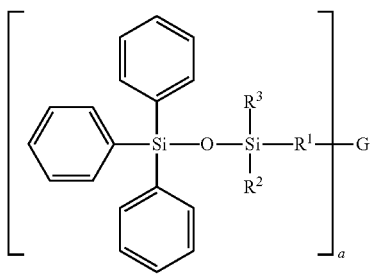

where each $R^2$ and each $R^3$ are independently selected from a monovalent hydrocarbon radical containing from 1 to about 8 carbon atoms, each $R^1$ is a divalent alkyl, alkene, arylene or alkyne group, each containing up to about 45 carbon atoms and G is hydrogen, an organic group or a silicon-containing group, and where subscript a is an integer of from 1 to 100.

11. The personal care composition of claim 10 wherein the silicone compound has a structure of general formula (I) where G is selected from the group consisting of:
(a) an organic group that is a linear or branched, unsaturated or saturated hydrocarbon radical containing up to about 1,000 carbon atoms, and optionally containing at least one of a heteroatom, a carbonyl group, an ester group, an amide group and a hydroxyl group with the valency of 1-25 subject to the limitation that the valance of the organic group is equal to the value of the subscript a;
(b) a cyclic siloxane with the general formula (II):

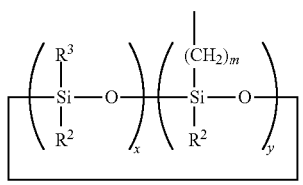

each $R^2$ and each $R^3$ are independently a monovalent hydrocarbon radical containing from 1 to about 8 carbon atoms, the subscript m is 2 to 6, the subscript x is 0-8 and the subscript y is 1-8, subject to the limitation that the value of subscript a=y; and, (c) a siloxane with the general formula (III):

$$M_b M^*_c D_d D^*_e T_f T^*_g Q_h A_i B_j C_k \quad (III)$$

where
$M=R^4R^5R^6SiO_{1/2}$,
$M^*=R^4R^*R^6SiO_{1/2}$
$D=R^7R^8SiO_{2/2}$,
$D^*=R^7R^*SiO_{2/2}$
$T=R^9SiO_{3/2}$,
$T^*=R^*SiO_{3/2}$,
$Q=SiO_{4/2}$,
$A=O_{1/2}Si(R^{10})(R^{11})R^{12}Si(R^{13})(R^{14})O_{1/2}$
$B=O_{1/2}Si(R^{15})(R^{16})R^{17}Si(R^{18})O_{2/2}$
$C=O_{1/2}Si(R^{19})(R^{20})R^{21}SiO_{3/2}$ where $R^4$, $R^5$, $R^6$, $R^7$, $R^8$, $R^9$, $R^{10}$, $R^{11}$, $R^{13}$, $R^{14}$, $R^{15}$, $R^{16}$, $R^{18}$, $R^{19}$, and $R^{20}$ are each independently selected from the group consisting of $OR^{22}$ and a monovalent hydrocarbon radical containing from 1 to about 20 carbon atoms, optionally containing at least one of a heteroatom, an aromatic group, and a hydroxyl group, $R^{12}$, $R^{17}$, and $R^{21}$ are independently a divalent hydrocarbon group of from 1 to about 8 carbon atoms, $R^{22}$ is a monovalent hydrocarbon radical containing from 1 to about 20 carbon atoms, $R^*$ is a divalent hydrocarbon where one of the valences is bound to $R^1$, and subscripts b, c, d, e, f, g, h, i, j and k are zero or positive subject to the limitation that $b+c+d+e+f+g+h+i+j+k<1000$ and $c+e+g\geq 1$ and $c+e+g=a$.

12. The personal care composition of claim 10 wherein the silicon-containing group is a silicone-containing group.

13. The personal care composition of claim 10 wherein the general formula (I) is such that a=1 and G is a linear or branched unsaturated hydrocarbon radical of up to 8 carbon atoms.

14. The personal care composition of claim 10 wherein the silicone compound is of the formula (IV):

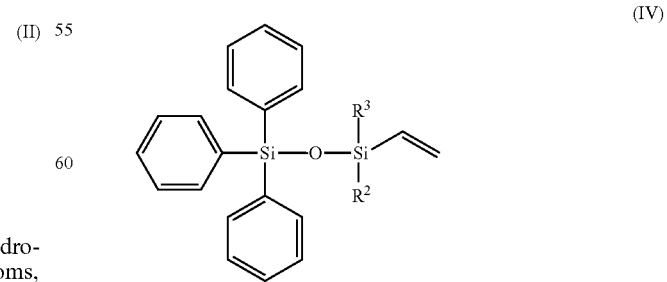

wherein $R^2$ and $R^3$ are each independently an alkyl group of from 1 to 3 carbon atoms.

15. The personal care composition of claim 11 wherein the silicone compound is of the general formula (III) and where the subscripts i+f+j≥1.
16. The personal care composition of claim 11 wherein the silicone compound is selected from the group consisting of:
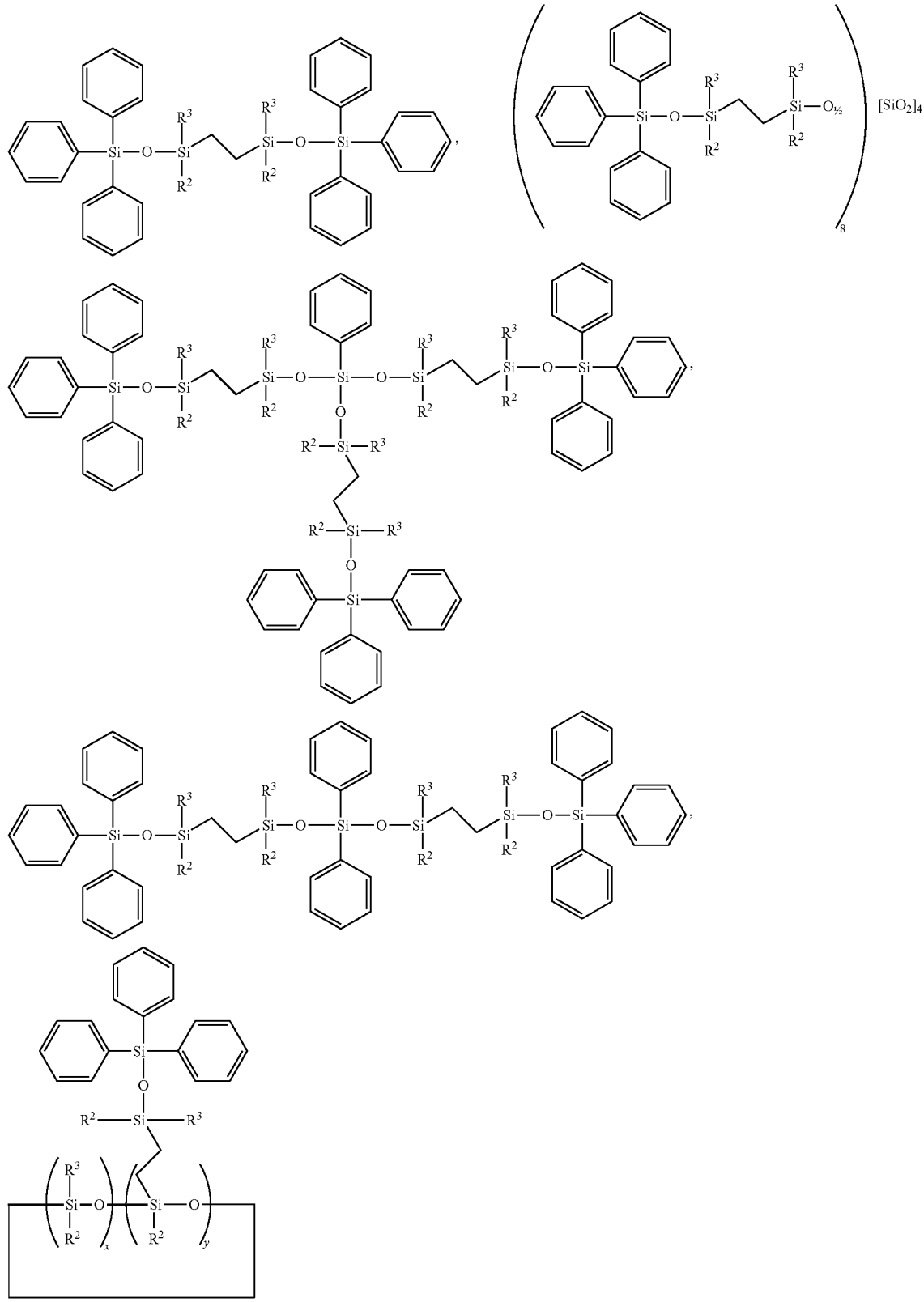

where x is 2 and y is 2,
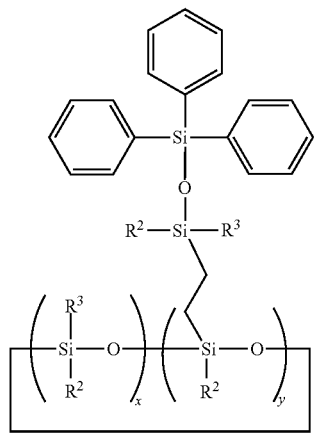
where x is 1 and y is 3, and
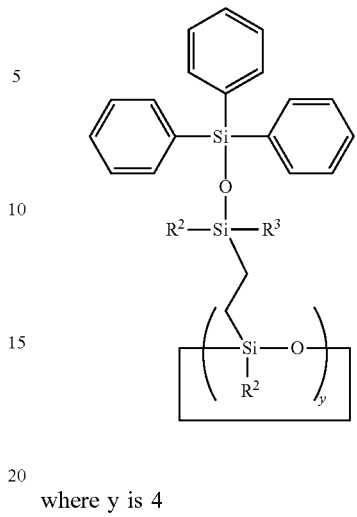
where y is 4
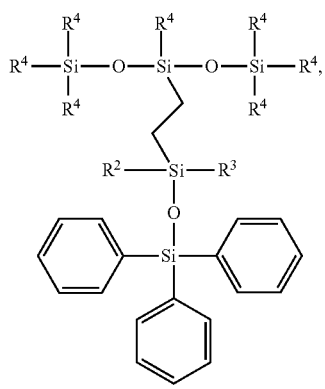
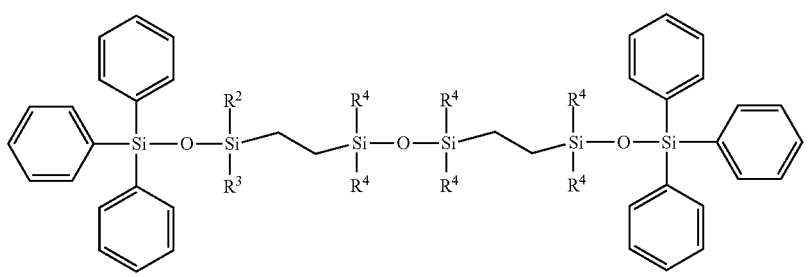
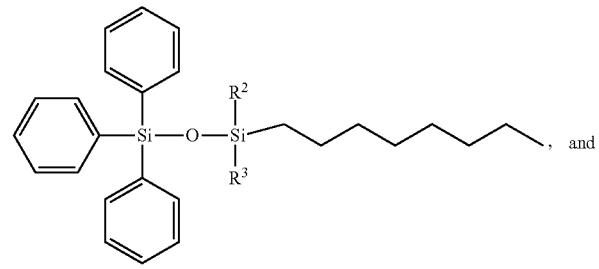, and
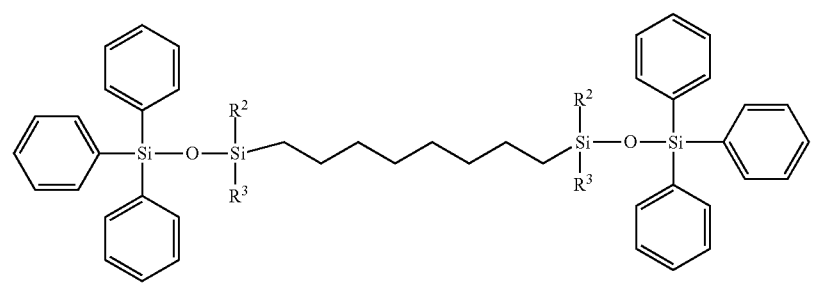

wherein in the foregoing formulae each $R^2$, $R^3$ and $R^4$ are each independently a monovalent hydrocarbon radical containing up to about 6 carbon atoms.

17. The personal care composition of claim 16 wherein each $R^2$, $R^3$ and $R^4$ is methyl.

18. The personal care composition of claim 10 wherein the silicone compound has a refractive index of greater than 1.50.

19. The personal care composition of claim 10 wherein the silicone compound has surface tension higher than 27 dynes/cm.

20. A sun care application comprising the silicone compound of claim 1 wherein the silicone compound is present in an amount effective to increase the SPF of the sun care application.

21. A personal care application comprising the silicone compound of claim 1 wherein the personal care application is selected from the group consisting of skin care products, sun care products, color cosmetic products, hair care products and luster enhancers.

22. A personal care application comprising the silicone compound of claim 1 which is an aqueous emulsion.

23. A personal care application comprising the silicone compound of claim 1 which is a non-aqueous emulsion.

24. A personal care application comprising the silicone compound of claim 1 wherein the personal care application is selected from the group consisting of deodorants, antiperspirants, antiperspirant/deodorants, shaving products, skin lotions, moisturizers, toners, bath products, cleansing products, hair care products, manicure products, protective creams, color cosmetics and other personal care formulations where silicone components have been conventionally added, as well as drug delivery systems for topical application of medicinal compositions that are to be applied to the skin.

25. The personal care application of claim 24 further comprising at least one personal care ingredient selected from the group consisting of emollients, moisturizers, humectants, pigments, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, volatile silicones, organic oils, waxes, film formers, thickening agents particulate fillers, and clays.

26. A process of making a 1,1,1-triphenyl-3,3-dialkyl-3-alkenyldisiloxane comprising reacting triphenylsilanol with a 1,1,3,3-tetralkyl-1,3-dialkenyldisilazane and/or an alkenyldialkylhalosilane to produce 1,1,1-triphenyl-3,3-dialkyl-3-alkenyldisiloxane, wherein each of the alkyl groups independently contain from 1 to 6 carbon atoms and each of the alkenyl groups independently contain from 2 to 4 carbon atoms.

27. A process of making the silicone compound of claim 1, wherein the process comprises:
  reacting 1,1,1-triphenyl-3,3-dialkyl-3-alkenyldisiloxane with a hydrogen siloxane to produce the silicone compound of the general formula (I).

28. A process of making the silicone compound of claim 1, wherein the process comprises reacting a 1,1,1-triphenyl-3,3-dialkyl-3-hydride disiloxane with an alkenyl compound containing from 2 to 10 carbon atoms.

* * * * *